(12) United States Patent
Nguyen et al.

(10) Patent No.: US 11,826,495 B2
(45) Date of Patent: Nov. 28, 2023

(54) BIODEGRADABLE PIEZOELECTRIC ULTRASONIC TRANSDUCER SYSTEM

(71) Applicant: University of Connecticut, Farmington, CT (US)

(72) Inventors: Thanh Duc Nguyen, South Windsor, CT (US); Thinh Le, Willington, CT (US); Eli Curry, North Franklin, CT (US)

(73) Assignee: University of Connecticut, Farmington, CT (US)

( * ) Notice: Subject to any disclaimer, the term of this patent is extended or adjusted under 35 U.S.C. 154(b) by 694 days.

(21) Appl. No.: 16/806,885

(22) Filed: Mar. 2, 2020

(65) Prior Publication Data

US 2020/0276365 A1 Sep. 3, 2020

Related U.S. Application Data

(60) Provisional application No. 62/812,491, filed on Mar. 1, 2019.

(51) Int. Cl.
*A61L 31/14* (2006.01)
*A61L 31/02* (2006.01)
(Continued)

(52) U.S. Cl.
CPC .......... *A61L 31/148* (2013.01); *A61L 31/022* (2013.01); *A61L 31/06* (2013.01); *A61L 31/10* (2013.01); *A61M 37/0092* (2013.01); *B06B 1/0696* (2013.01); *H02J 50/12* (2016.02);

*H02J 50/20* (2016.02); *H10N 30/02* (2023.02); *H10N 30/078* (2023.02); *H10N 30/1061* (2023.02);
(Continued)

(58) Field of Classification Search
CPC . B06B 1/0696; H10N 30/875; H10N 30/1061
See application file for complete search history.

(56) References Cited

U.S. PATENT DOCUMENTS

| 589,119 A | 8/1897 | Burgess | |
|---|---|---|---|
| 4,198,987 A * | 4/1980 | Cain | .................. A61B 8/4472 600/457 |

(Continued)

FOREIGN PATENT DOCUMENTS

| CN | 102657914 B | 5/2015 |
|---|---|---|
| CN | 106109792 A | 11/2016 |

(Continued)

OTHER PUBLICATIONS

Curry et el. Biodegradable Piezoelectric Force Sensor. PNAS. Jan. 2018. vol. 115. No. 5. pp 909-9014 (Year: 2018).*

(Continued)

*Primary Examiner* — Cachet I Proctor
(74) *Attorney, Agent, or Firm* — Michael Best & Friedrich LLP

(57) ABSTRACT

A biodegradable and biocompatible piezoelectric nanofiber platform for medical implant applications, including a highly sensitive, wireless, biodegradable force sensor for the monitoring of physiological pressures, and a biodegradable ultrasonic transducer for the delivery of therapeutics or pharmaceuticals across the blood-brain barrier.

11 Claims, 12 Drawing Sheets
(12 of 12 Drawing Sheet(s) Filed in Color)

(51) Int. Cl.

| | | |
|---|---|---|
| *A61L 31/10* | (2006.01) | |
| *A61L 31/06* | (2006.01) | |
| *B06B 1/06* | (2006.01) | |
| *H02J 50/12* | (2016.01) | |
| *H02J 50/20* | (2016.01) | |
| *A61M 37/00* | (2006.01) | |
| *H10N 30/02* | (2023.01) | |
| *H10N 30/078* | (2023.01) | |
| *H10N 30/857* | (2023.01) | |
| *H10N 30/87* | (2023.01) | |
| *H10N 30/00* | (2023.01) | |
| *A61B 8/12* | (2006.01) | |

(52) U.S. Cl.
CPC ......... *H10N 30/857* (2023.02); *H10N 30/875* (2023.02); *A61B 8/12* (2013.01); *A61L 2420/02* (2013.01); *A61M 2205/04* (2013.01)

(56) References Cited

U.S. PATENT DOCUMENTS

| | | |
|---|---|---|
| 4,438,773 A | 3/1984 | Letterio |
| 5,131,276 A | 7/1992 | Kibblewhite |
| 5,246,013 A | 9/1993 | Frank et al. |
| 5,287,331 A | 2/1994 | Schindel et al. |
| 5,306,620 A | 4/1994 | Ginsberg et al. |
| 5,443,495 A | 8/1995 | Buscemi et al. |
| 5,498,499 A | 3/1996 | Flow et al. |
| 5,512,600 A | 4/1996 | Mikos et al. |
| 5,514,378 A | 5/1996 | Mikos et al. |
| 5,678,565 A | 10/1997 | Sarvazyan |
| 5,697,901 A | 12/1997 | Eriksson |
| 5,794,023 A | 8/1998 | Hobbs et al. |
| 5,827,198 A | 10/1998 | Kassal |
| 5,967,989 A * | 10/1999 | Cimochowski ...... A61B 5/6862 128/903 |
| 6,142,948 A | 11/2000 | Toda |
| 6,219,574 B1 | 4/2001 | Cormier et al. |
| 6,334,856 B1 | 1/2002 | Allen et al. |
| 6,447,887 B1 | 9/2002 | Claus et al. |
| 6,468,219 B1 | 10/2002 | Njemanze |
| 6,627,421 B1 | 9/2003 | Unger et al. |
| 6,835,377 B2 | 12/2004 | Goldberg et al. |
| 7,001,372 B2 | 2/2006 | Richter |
| 7,184,826 B2 | 2/2007 | Cormier et al. |
| 7,332,197 B2 | 2/2008 | Wood et al. |
| 7,344,499 B1 | 3/2008 | Prausnitz et al. |
| 7,396,537 B1 | 7/2008 | Krupnick et al. |
| 7,879,093 B2 | 2/2011 | Wei et al. |
| 7,906,223 B2 | 3/2011 | Rakow et al. |
| 8,067,110 B2 | 11/2011 | Rakow et al. |
| 8,162,901 B2 | 4/2012 | Gonnelli et al. |
| D659,820 S | 5/2012 | Abel et al. |
| 8,301,262 B2 | 10/2012 | Mi et al. |
| 8,469,936 B2 | 6/2013 | Robinson et al. |
| 8,708,966 B2 | 4/2014 | Allen et al. |
| 8,798,932 B2 | 8/2014 | Boyden et al. |
| 8,946,974 B2 | 2/2015 | Yu et al. |
| 8,955,515 B2 | 2/2015 | Rakow et al. |
| 9,040,087 B2 | 5/2015 | Boyden et al. |
| 9,050,053 B2 | 6/2015 | Morgan |
| 9,089,677 B2 | 7/2015 | Soo et al. |
| 9,192,655 B2 | 11/2015 | Arinzeh et al. |
| 9,381,680 B2 | 7/2016 | Oh et al. |
| 9,444,030 B2 | 9/2016 | Wang et al. |
| 9,527,257 B2 | 12/2016 | Lipton et al. |
| 9,795,774 B2 | 10/2017 | Takada et al. |
| 9,846,091 B2 | 12/2017 | Lu et al. |
| 9,849,270 B2 | 12/2017 | Stockholm |
| 9,949,035 B2 * | 4/2018 | Rucker ................ H04R 17/00 |
| 10,004,790 B2 | 6/2018 | D'Souza |
| 10,098,574 B1 | 10/2018 | Kam |
| 10,245,421 B2 | 4/2019 | Ross |
| 10,292,831 B2 | 5/2019 | Zellmer et al. |
| 10,500,300 B2 | 12/2019 | Dybe et al. |
| 10,617,880 B2 | 4/2020 | Zellmer et al. |
| 10,632,653 B2 | 4/2020 | Niitsu et al. |
| 10,710,011 B2 | 7/2020 | Inoue et al. |
| 2002/0081732 A1 | 6/2002 | Bowlin et al. |
| 2002/0082543 A1 | 6/2002 | Park et al. |
| 2004/0015211 A1 | 1/2004 | Nurmikko et al. |
| 2004/0018226 A1 | 1/2004 | Wnek et al. |
| 2004/0028655 A1 | 2/2004 | Nelson et al. |
| 2005/0248547 A1 | 11/2005 | Kent et al. |
| 2006/0043843 A1 | 3/2006 | Sugiura et al. |
| 2006/0050189 A1 | 3/2006 | Ito et al. |
| 2006/0107749 A1 | 5/2006 | Liu et al. |
| 2006/0190080 A1 | 8/2006 | Danoff et al. |
| 2006/0224237 A1 | 10/2006 | Furst et al. |
| 2007/0141106 A1 | 6/2007 | Bonutti et al. |
| 2007/0225631 A1 | 9/2007 | Bowlin et al. |
| 2007/0255422 A1 | 11/2007 | Wei et al. |
| 2007/0270738 A1 | 11/2007 | Wu et al. |
| 2007/0293912 A1 | 12/2007 | Cowan et al. |
| 2008/0009802 A1 | 1/2008 | Lambino et al. |
| 2008/0058633 A1 | 3/2008 | Boyden et al. |
| 2008/0269666 A1 | 10/2008 | Wang et al. |
| 2009/0030365 A1 | 1/2009 | Tokumoto et al. |
| 2009/0062723 A1 | 3/2009 | Skiba |
| 2009/0163965 A1 | 6/2009 | Boyden et al. |
| 2009/0182306 A1 | 7/2009 | Lee et al. |
| 2009/0192431 A1 | 7/2009 | Horstmann et al. |
| 2009/0280153 A1 | 11/2009 | Hunter et al. |
| 2010/0152644 A1 | 6/2010 | Pesach et al. |
| 2011/0028905 A1 | 2/2011 | Takada |
| 2011/0109204 A1 | 5/2011 | Tajitsu et al. |
| 2011/0230747 A1 | 9/2011 | Rogers et al. |
| 2011/0242310 A1 | 10/2011 | Beebe et al. |
| 2012/0197155 A1 | 8/2012 | Mattes et al. |
| 2012/0226295 A1 | 9/2012 | Jabbari |
| 2013/0005708 A1 | 1/2013 | Lalwani |
| 2013/0041244 A1* | 2/2013 | Woias ................ G01L 1/142 600/381 |
| 2013/0086703 A1 | 4/2013 | Maruyama et al. |
| 2013/0140649 A1 | 6/2013 | Rogers et al. |
| 2014/0005606 A1 | 1/2014 | Chen et al. |
| 2014/0145365 A1 | 5/2014 | Omenetto et al. |
| 2014/0333184 A1* | 11/2014 | Wang ................ H01L 41/193 310/365 |
| 2015/0073551 A1 | 3/2015 | Uehlin |
| 2015/0134061 A1 | 5/2015 | Friis et al. |
| 2015/0165020 A1 | 6/2015 | Jaklenec et al. |
| 2015/0236242 A1* | 8/2015 | Ryu ................ H10N 30/1061 310/313 C |
| 2016/0005951 A1 | 1/2016 | Yoshida et al. |
| 2016/0050750 A1 | 2/2016 | Rogers et al. |
| 2016/0067375 A1 | 3/2016 | Holmes et al. |
| 2016/0095599 A1 | 4/2016 | Jose et al. |
| 2016/0175408 A1 | 6/2016 | Chang et al. |
| 2016/0184571 A1 | 6/2016 | Admati |
| 2016/0184595 A1 | 6/2016 | Hossainy |
| 2016/0190427 A1 | 6/2016 | Kim et al. |
| 2016/0287668 A1 | 10/2016 | Tankovich |
| 2017/0020402 A1* | 1/2017 | Rogers ................ A61B 5/0031 |
| 2017/0027168 A1 | 2/2017 | Heath |
| 2017/0080196 A1 | 3/2017 | Lee et al. |
| 2017/0179370 A1 | 6/2017 | Kim et al. |
| 2017/0189660 A1 | 7/2017 | Baek |
| 2017/0252546 A1 | 9/2017 | Park et al. |
| 2017/0258738 A1 | 9/2017 | DeMuth et al. |
| 2017/0268942 A1 | 9/2017 | Pedder et al. |
| 2017/0306295 A1 | 10/2017 | Hazot et al. |
| 2017/0368321 A1 | 12/2017 | Baek |
| 2018/0055643 A1 | 3/2018 | Castro et al. |
| 2018/0140817 A1 | 5/2018 | Spector |
| 2018/0256905 A1* | 9/2018 | Francia ................ A61N 1/3956 |
| 2018/0289616 A1 | 10/2018 | Chen et al. |
| 2018/0325806 A1 | 11/2018 | Litvack et al. |
| 2019/0142318 A1 | 5/2019 | Diebold et al. |
| 2019/0209819 A1 | 7/2019 | Ross |
| 2019/0217071 A1 | 7/2019 | Engel et al. |
| 2019/0269895 A1 | 9/2019 | Nguyen et al. |
| 2019/0307697 A1 | 10/2019 | Ma et al. |

(56) References Cited

U.S. PATENT DOCUMENTS

| | | |
|---|---|---|
| 2019/0319181 A1 | 10/2019 | Melandso et al. |
| 2019/0328285 A1 | 10/2019 | Liu |
| 2019/0330771 A1 | 10/2019 | Takumi et al. |
| 2020/0009767 A1 | 1/2020 | Li |
| 2020/0093966 A1 | 3/2020 | Rabolt et al. |
| 2020/0276018 A1 | 9/2020 | Nguyen et al. |
| 2020/0282350 A1 | 9/2020 | Inoue et al. |
| 2020/0292206 A1 | 9/2020 | Tamakura et al. |
| 2020/0313066 A1 | 10/2020 | Getman |
| 2021/0127998 A1 | 5/2021 | Nguyen et al. |
| 2021/0283387 A1 | 9/2021 | Silbart et al. |
| 2021/0378949 A1 | 12/2021 | Nguyen et al. |
| 2021/0379249 A1 | 12/2021 | Nguyen et al. |
| 2022/0096371 A1 | 3/2022 | Nguyen et al. |
| 2022/0176171 A1 | 6/2022 | Nguyen et al. |

FOREIGN PATENT DOCUMENTS

| | | | |
|---|---|---|---|
| EP | 0955359 B1 | 1/2009 | |
| EP | 1993621 B1 | 8/2011 | |
| EP | 1715915 B1 | 11/2012 | |
| EP | 2482772 B1 | 10/2018 | |
| EP | 3542740 A1 | 9/2019 | |
| IN | 202041031484 A | 7/2020 | |
| KR | 101832716 B1 | 2/2018 | |
| RU | 2082467 C1 | 6/1997 | |
| WO | WO2006057987 A1 | 6/2006 | |
| WO | WO2008085904 A1 | 7/2008 | |
| WO | WO-2008085904 A1 * | 7/2008 | ............. B82Y 10/00 |
| WO | WO 2012103257 A2 | 8/2012 | |
| WO | WO 2012127224 A1 | 9/2012 | |
| WO | WO 2013101908 A1 | 7/2013 | |
| WO | WO 2014143412 A8 | 11/2014 | |
| WO | 2017003238 A1 | 1/2017 | |
| WO | WO2017011320 A1 | 1/2017 | |
| WO | WO 2017139253 A1 | 8/2017 | |
| WO | WO 2017151715 A1 | 9/2017 | |
| WO | WO-2017191542 A1 * | 11/2017 | ........... A61F 2/1635 |
| WO | WO 2018017196 A1 | 1/2018 | |
| WO | WO 2018089918 A1 | 5/2018 | |
| WO | WO 2018114871 A1 | 6/2018 | |
| WO | WO 2018170132 A1 | 9/2018 | |
| WO | WO 2019025625 A1 | 2/2019 | |
| WO | WO 2019094349 A1 | 5/2019 | |
| WO | 2019143293 A1 | 7/2019 | |

OTHER PUBLICATIONS

Curry et al. Supporting Information Appendix. Biodegradable Piezoelectic Force Sensor. PNAS. Jan. 2018 pp. 1-33 (Year: 2018).*

Zhang et al., "Piezoelectric polymer multilayer on flexible substrate for energy harvesting," IEEE Transactions on Ultrasonics, Ferroelectrics, and Frequency Control, 2013, 60(9):2013-2020.

Ramadan et al., "A review of piezoelectric polymers as functional materials for electromechanical transducers," Smart Materials and Structures 23, 2014, 033001.

Dagdeviren et al., "Recent progress in flexible and stretchable piezoelectric devices for mechanical energy harvesting, sensing and actuation," Extreme Mechanics Letters, 2016, 9(1):269-281.

European Patent Office Extended Search Report for Application No. 18767093.0 dated Nov. 27, 2020 (13 pages).

Amini et al., "Bone tissue engineering: recent advances and challenges," Critical Reviews ™ in Biomedical Engineering, 2012, 40,(5):363-408.

Anglen, "The clinical use of bone stimulators," Journal of the Southern Orthopaedic Association, 2002, 12, (2), 46-54.

Bauer et al., "Bone Graft Materials: An Overview of the Basic Science," Clinical orthopaedics and related research, 2000, 371, 10-27.

Bussemer et al., "Pulsatile drug-delivery systems," Crit Rev Ther Drug Syst., 2001, 18(5):433-458, Abstract.

Carpentier et al., "Clinical trial of blood-brain barrier disruption by pulsed ultrasound," Science translational medicine, 2016, 8(343):343re2, 9 pages.

Chen et al., "Fully embeddable chitosan microneedles as a sustained release depot for intradermal vaccination," Biomaterials, 2013, 34(12):3077-3086.

Chiappini et al., "Biodegradable silicon nanoneedles delivering nucleic acids intracellularly induce localized in vivo neovascularization," Nature Materials, 2015, 14:532-539.

Cohen et al., "Totally implanted direct current stimulator as treatment for a nonunion in the foot," The Journal of foot and ankle surgery: official publication of the American College of Foot and Ankle Surgeons, 1993, 32, (4), 375-381.

Csafeglobal, The Cost of a Broken Vaccine Cold Chain Part Two, Financial Cost. <http://csafeglobal.com/the-cost-of-a-broken-vaccine-cold-chain-part-two-financial-cost-1> Sep. 17, 2014, 3 pages.

Curry et al., "Biodegradable piezoelectric force sensor," PNAS, 2018, 115(5):909-914.

Dai et al., "Electrospun emodin polyvinylpyrrolidone blended nanofibrous membrane: a novel medicated biomaterial for drug delivery and accelerated wound healing," Journal of Materials Science: Materials in Medicine, 2012, 23(11):2709-2716.

Demiray, "Electro-mechanical remodelling of bones," International Journal of Engineering Science, 1983, 21, (9), 1117-1126.

Ferreira et al., "Bone Collagen Role in Piezoelectric Mediated Remineralization," Acta Microscopica, 2009, 18(3):278-286.

Glazner et al., "Cost of vaccine administration among pediatric practices," Pediatrics, 2009, 124(Supplement 5):S492-S498.

Graf et al., "In Stimulation of bone growth by implanted FEP electrets and PVDF piezoelectric films," Proceedings 5th International Symposium on Electrets (ISE 5), Heidelberg, 1985, pp. 813-818.

Habibovic, "Strategic directions in osteoinduction and biomimetics," Tissue Engineering Part A, 2017, 23, (23-24), 1295-1296.

Laurencin et al., "Bone graft substitutes," Expert Review of Medical Devices, 2006, 3(1):49-57.

Laurencin et al., "Regenerative engineering," Science translational medicine, 2012, 4(160): 160ed9, 4 pages.

Laurencin et al., "Tissue engineering: orthopedic applications," Annual review of biomedical engineering, 1999, 1, (1), 19-46.

Madlon-Kay et al., "Too many shots? Parent, nurse, and physician attitudes toward multiple simultaneous childhood vaccinations," Archives of Family Medicine, 1994, 3(7):610-13.

McHugh et al., Fabrication of fillable microparticles and other complex 3D microstructures, Science, 2017, 357(6356):1138-1142.

McHugh et al., "Single-injection vaccines: Progress, challenges, and opportunities," Journal of Controlled Release, 2015, 219:596-609.

Meng et al., "A Hybrid Inductive-Ultrasonic Link for Wireless Power Transmission to Millimeter-Sized Biomedical Implats," IEEE Transactions on Circuits and Systems—II: Express Briefs, 2017, 64(10):1137-1141.

Narayanan et al., "Poly (lactic acid)-based biomaterials for orthopaedic regenerative engineering," Advanced drug delivery reviews, 2016, 107, 247-276.

Nguyen et al., "Piezoelectric nanoribbons for monitoring cellular deformations," Nature Nanotechnology, 2012, 7:587-593.

Poeggel et al., "Optical Fibre Pressure Sensors in Medical Applications," Sensors, 2015, 15(7):17115-17148.

Rolland et al., "Direct fabrication and harvesting of monodisperse, shape-specific nanobiomaterials," Journal of the American Chemical Society, 2005, 127(28):10096-10100.

Sanni et al., "Inductive and Ultrasonic Multi-Tier Interface for Low-Power, Deeply Implantable Medical Devices," IEEE Transactions on Biomedical Circuits and Systems, 2012, 6(4):297-308.

Shende et al., Micro to nanoneedles: a trend of modernized transepidermal drug delivery system, Artificial Cells, Nanomedicine, and Biotechnology, 2017, 8 pages.

Simonelli et al., "Dissolution rates of high energy polyvinylpyrrolidone (PVP)-sulfathiazole coprecipitates," Journal of pharmaceutical sciences, 1969, 58(5):538-549.

Soltman et al., "Inkjet-printed line morphologies and temperature control of the coffee ring effect," Langmuir, 2008, 24(5):2224-2231.

(56) References Cited

OTHER PUBLICATIONS

Sullivan et al., "Dissolving polymer microneedle patches for influenza vaccination," Nature medicine, 2010, 16(8):915-921.
Tanimoto et al., "Effect of helix inversion of poly(ß-phenethyl I-aspartate) on macroscopic piezoelectricity," Japanese Journal of Applied Physics, 2014, 53(9S):09PC01.
Vaers, Vaccine Adverse Event Reporting System. <https://vaers.hhs.gov/data/index> webpage available as early as Oct. 9, 2009, 2 pages.
Xu et al., "Future of the particle replication in nonwetting templates (PR.INT) technology," Angewandte Chemie International Edition, 2013, 52(26):6580-6589.
Yu et al., "Oral fast-dissolving drug delivery membranes prepared from electrospun polyvinylpyrrolidone ultrafine fibers," Nanotechnology, 2009, 20(5):055104, 9 pages.
International Search Report and Written Opinion for Application No. PCT/US2019/020838 dated Jun. 26, 2019 (14 pages).
Ando et al., "Pressure-sensitive touch panel based on piezoelectric poly (I-lactic acid) film", 2013, Jpn. J. Appl. Phys. 52:09KD17.
Bello et al., "Development of a smart pump for monitoring and controlling intraocular pressure", Ann Biomed Eng 45:990-1002, 2017.
Bos et al., "Resorbable poly(L-lactide) plates and screws for the fixation of zygomatic fractures", 1987, J Oral Maxillofac Surg, 45:751-753.
Chee et al., "An investigation of array of piezoelectric transducer for raindrop energy harvesting application", 2016, IEEE Region Tenth Conference, pp. 3771-3774.
Lee et al., "Micromachined piezolectric force senors based on PZT thin films", 1996, IEEE Trans Ultrason Farroelectri Freq Control, 43:553-559.
Di Mario et al., "Drug-eluting bioabsorbable magnesium stent", 2004, J Interv Cardiol., 17:391-395.
Fukada, "New Piezoelectric polymers" 1998, Jpn J Appl Phys 37:2775-2780.
Ewald et al., "Monitoring of vital signs for long-term survival of mice under anesthesia", 2011, Cold Spring Harb Protoc. 2011:pdb.prot5563.
Guo et al., "Measurements of piezoelectric coefficient d33 of lead zirconate titanate thin films using a mini force hammer", 2013, J Vib Accoust, 135:011003.
Jayson et al., "Intra-articular pressure in rheumatoid arthritis of the knee 3. Pressure changes during joint use", Ann Rheum Dis, 1970, 29:401-408.
Kang et al., "Bioresorbable silicon electronic sensors for the brain", Nature, 2016, 530:71-76.
Liu et al., "Design and development of three-dimensional scaffolds for tissue engineering", 2007, Chem Eng Res Des, 85:1051-1064.
Maloney et al., "Intracranial pressure monitoring in acute liver failure: Institutional case series", 2016, Neurocrit Care 25:86-93.
Ando et al., "Film sensor device fabricated by a piezoelectric poly(L-lactic acid) film", 2012, Jpn J Appl Phys 51:09LD14.
Minary-Jolandan et al., "Nanoscale characterization of isolated individual type I collagen fibrils: Polarization and piezoelectricity", 2009, Nanotechnology 20:085706.
Nguyen et al., "Wafter-scale nanopatterning and translation into high-performance piezoelectric nanowires", 2010, Nano Lett 10:4595-4599.
Nguyen, et al., "Bionics in tissue engineering" 2017, Tissue Engineering for Artifical Organs, pp. 677-669.
Qi et al., "Enhanced piezoelectricity and stretchability in energy harvesting devices fabricated from buckled PZT ribbons", 2011, Nano Lett. 11:1331-1336.
Qi et al., "Stretchable piezoelectric nanoribbons for biocompatible energy harvesting", Stretchable Electrionics, pp. 111-139.
Ru et al., "Dominant B-form of poly(I-lactic acid) obtained directly from melt under shear and pressure fields", 2016, Macromolecules 49:3826-3837.
Saravanos et al., "Layerwise mechanics and finite element for the dynamic analysis of piezoelectric composite plates", 1997, Int J Solids Struct 34:359-378.
Sawano et al., "New design of actuator using shear piezoelectricity of a chiral polymer, and prototype device", 2010, Polym. Int. 59: 365-370.
Seol et al., "Hysteretic behavior of contact force response in triboelectric nanogenerator", 2017, Nano Energy 32:408-413.
Sinderby et al., "Diaphragm activation during exercise in chronic obstructive pulmonary disease", 2001, Am J Respir Crit Care Med, 163:1637-1641.
Syuhei et al., "Sensing using piezoelectric chiral polymer fiber", 2012, Jpn. J. Appl. Phys. 51:09LD16.
Tajitsu et al., "Microactuators with piezoelectric polylactic acid fibers—toward the realizaation of tweezers for biological cells", 2004, Ferroelectrics 304:195-200.
Talmor et al., "Mechanical ventilation guided by esophageal pressure in acute lung injury", N. Engl. J Med., 2008, 359, 2095-2104.
Xu et al., "Improvements of thermal property and crystallization behavior of PLLA based multiblock copolymer by forming sterocomplex with PDLA oligomer", 2006, Polymer (Guildf), 47:3922-3928.
Yoshida et al., "High piezoelectric performance of poly (lactic acid) film manufactured by solid state extrusion", 2014, Jpn. J. Appl. Phys. 53:09PC02.
Yoshida et al., "Piezoelectric motion of multilayer film with alternate rows of optical isomers of chiral polymer film", 2011, Jpn J Appl Phys 50:09ND13.
Zheng et al., "Biodegradable triboelectric nongenerator as a lifetime designed implantable power source", 2016, Sci Adv 2:e1501478.
Zi et al., "Triboelectric-pyroelectric-piezoelectric hybrid cell for high-efficiency energy-harvesting and self-powered sensing", Adv Mater 27:2340-2347, 2015.
D'Lima et al. "Implantable sensor technology: measuring bone and joint biomechanics of daily life in vivo", Arthritis Reseasrch and Therapy, 2013, 15: 203.
Klosterhoff et al., "Implantable Sensors for Regenerative Medicine", Journal of Biomechanical Engineering, ASME Feb. 2017, vol. 139, 021009-1.
International Preliminary Report on Patentability for Application No. PCT/US2018/022441 dated Sep. 17, 2019 (10 pages).
European Patent Office Extended Search Report for Application No. 19764864 dated Mar. 22, 2022 (11 pages).
ABCAM. Elisa kit for MCP-1. https://www.abcam.com/rat-mcp1-elisa-kit-ab219045.html. Accessed Aug. 22, 2022 (5 pages).
ABCAM. Elisa kit for TNF-alpha. https://www.abcam.com/rat-tnf-alpha-elisa-kit-ab236712.html. Accessed Aug. 22, 2022 (5 pages).
AFPRO Filters. Pm1: The Most Hazardous Kind of Particulate Matter. https://web.archive.org/web/20200609213853/https://www.afprofilters.com/pm1-airfilter/, Jun. 9, 2020, (4 pages).
Ager, D. J. et al. Stability of aspirin in solid mixtures. Journal of pharmaceutical sciences 1986, 75, (1), 97-101.
Alemdaroğlu, C.; et al. An investigation on burn wound healing in rats with chitosan gel formulation containing epidermal growth factor. Burns 2006, 32, (3), 319-327.
Alneami AQ, et al. Effect of Electrical Current Stimulation on Pseudomonas Aeruginosa Growth. Journal of Physics: Conference Series. 2018;1003:012112.
Amirnasr, E. et al. Basis Weight Uniformity Analysis in Nonwovens. The Journal of The Textile Institute 2014, 105 (4), 444-453.
Ando et al., "New human machine interface devices using a piezoelectric poly(L-lactic acid) film" in 2013 IEEE International Symposium on the Applications of Ferroelectric and Workshop on the Piezoresponse Force Microscopy (ISAF/PFM) (IEEE, 2013), pp. 236-239.
Arakha M, et al. The effects of interfacial potential on antimicrobial propensity of ZnO nanoparticle. Scientific Reports. 2015;5(1):9578.
Asadi MR, et al. Bacterial Inhibition by Electrical Stimulation. Advances in Wound Care. 2013;3(2):91-97.
Atkins et al. Raman spectroscopy of blood and blood components. Appl. Spectrosc. 71, 767-793 (2017).
Babu, R. et al. Assessment of skin irritation and molecular responses in rat skin exposed to nonane, dodecane and tetradecane. Toxicology letters 2004, 153, (2), 255-266.

(56) References Cited

OTHER PUBLICATIONS

Bai, Y.; et al. Washable Multilayer Triboelectric Air Filter for Efficient Particulate Matter Pm2. 5 Removal. Advanced Functional Materials 2018, 28 (15), 1706680.
Baker, B., et al. Electrical stimulation of articular cartilage regeneration. Annals of the New York Academy of Sciences 238, 491-499 (1974).
Banerjee J, et al. Silver-zinc redox-coupled electroceutical wound dressing disrupts bacterial biofilm. PLoS One. 2015;10(3):e0119531-e0119531.
Barbour, K. E.; et al., Prevalence of doctor-diagnosed arthritis and arthritis-attributable activity limitation—United States, 2010-2012. MMWR. Morbidity and mortality weekly report 2013, 62, (44), 869-873.
Barbour, K. E.; et al., Vital signs: prevalence of doctor-diagnosed arthritis and arthritis-attributable activity limitation—United States, 2013-2015. MMWR. Morbidity and mortality weekly report 2017, 66, (9), 246-253.
Barki KG, et al. Electric Field Based Dressing Disrupts Mixed-Species Bacterial Biofilm Infection and Restores Functional Wound Healing. Ann Surg. 2019;269(4).
Barton, N. J.; et al., Demonstration of a novel technique to quantitatively assess inflammatory mediators and cells in rat knee joints. Journal of Inflammation 2007, 4, (1), 13.
Bastaki, S. M.; et al. Effect of Aspirin and ibuprofen either alone or in combination on gastric mucosa and bleeding time and on serum prostaglandin E 2 and thromboxane A 2 levels in the anaesthetized rats in vivo. Molecular and cellular biochemistry 2018, 438, (1-2), 25-34.
Baur D, Gladstone BP, Burkert F, Carrara E, Foschi F, Dobele S, Tacconelli E: Effect of antibiotic stewardship on the incidence of infection and colonisation with antibiotic-resistant bacteria and Clostridium difficile infection: a systematic review and meta-analysis. Lancet Infect Dis 2017, 17(9):990-1001.
BCC Research—Global Markets for Drug-Device Combinations, Jan. 2015. PHM045D.
Beaudet J, Tulman ER, Pflaum K, Liao X, Kutish GF, Szczepanek SM, Silbart LK, Geary SJ: Transcriptional Profiling of the Chicken Tracheal Response to Virulent Mycoplasma gallisepticum Strain Rlow. Infect Immun 2017, 85(10).
Bergsma JE, et al. Late degradation tissue response to poly(1-lactide) bone plates and screws. Biomaterials. 1995;16(1):25-31.
Besinis, A.; et al. Antibacterial activity and biofilm inhibition by surface modified titanium alloy medical implants following application of silver, titanium dioxide and hydroxyapatite nanocoatings. Nanotoxicology 2017, 11, (3), 327-338.
Bir SC, et al. Control of angiogenesis dictated by picomolar superoxide levels. Free Radic Biol Med. 2013;63:135-142.
Blake KM, Carrigan SO, Issekutz AC, Stadnyk AW: Neutrophils migrate across intestinal epithelium using beta2 integrin (CD11b/CD18)-independent mechanisms. Clin Exp Immunol 2004, 136(2):262-268.
Bloomberg News. Mask Mandates by Nation: Most Still Await a Breath of Fresh Air. https://www.bloomberg.com/news/articles/2021-05-14/mask-mandates-by-nation-most-still-await-a-breath-of-fresh-air. May 14, 2021 (9 pages).
Boks NP, et al. Forces involved in bacterial adhesion to hydrophilic and hydrophobic surfaces. Microbiology. 2008;154(Pt 10):3122-3133.
Bose, S.; et al. A review on advances of sustained release drug delivery system. Int. Res. J. Pharm 2013, 4, 1-4.
Boster Bio. ELISA kit for IL-1 alpha. https://www.bosterbio.com/rat-il-1-alpha-picokine-trade-elisa-kit-ek0390- boster.html#bs_references. Jul. 1, 2013. Accessed on Aug. 22, 2022. (8 pages).
Bottino, M. C. et al. in Biomaterials for Oral and Craniomaxillofacial Applications vol. 17 90-100 (Karger Publishers, 2015).
Boutry et al., A stretchable and biodegradable strain and pressure sensor for orthopaedic application. Nat. Electron. 1, 314-321 (2018).
Boutry et al., Biodegradable and flexible arterial-pulse sensor for the wireless monitoring of blood flow. Nat. Biomed. Eng. 3, 47-57 (2019).
Bronaugh, R. L.; et al., Differences in permeability of rat skin related to sex and body site. J. Soc. Cosmet. Chem 1983, 34, (12), 127-135.
Brooks, J. T.; et al., Effectiveness of Mask Wearing to Control Community Spread of Sars-Cov-2. Jama 2021, 325 (10), 998-999.
Brune, K.; et al. Recent Insight into the Mechanism of Gastrointestinal Tract Ulceration. Scandinavian Journal of Rheumatology 1987, 16, (sup65), 135-140.
Byrne, J. D.; et al., Injection Molded Autoclavable, Scalable, Conformable (Imasc) System for Aerosol-Based Protection: A Prospective Single-Arm Feasibility Study. BMJ open 2020, 10 (7), e039120.
Caballe-Serrano, J. et al. On the search of the ideal barrier membrane for guided bone regeneration. Journal of clinical and experimental dentistry 10, e477 (2018).
Cadavid, A. P., Aspirin: the mechanism of action revisited in the context of pregnancy complications. Frontiers in immunology 2017, 8, 261.
Campbell, C. L. et al. Aspirin dose for the prevention of cardiovascular disease: a systematic review. Jama 2007, 297, (18), 2018-2024.
Carvalho, E. O., et al. "Tailoring bacteria response by piezoelectric stimulation." ACS applied materials & interfaces 11.30 (2019): 27297-27305.
Caspani, M. Delta Variant Pushes US Cases Hospitalizations 6 Month High. Aug. 9, 2021. https://web.archive.org/web/20210809174911/https://www.reuters.com/world/us/delta-variant-pushes-us-cases- hospitalizations-6-month-high-2021-08-09/ (12 pages).
CDC. Antibiotic resistance threats in the United States, 2019. US Department of Health and Human Services. 2019 (150 pages).
CDC. Implementing Filtering Facepiece Respirator (Ffr) Reuse, Including Reuse after Decontamination, When There Are Known Shortages of N95 Respirators. https://www.cdc.gov/coronavirus/2019-ncov/hcp/ppe-strategy/decontamination-reuse-respirators.html, Oct. 19, 2020, (10 pages).
CDC. Periodontal Disease. <https://www.cdc.gov/oralhealth/conditions/periodontal-disease.html> (Jul. 10, 2013) (3 pages).
CDC. Personal Protective Equipment: Questions and Answers. https://www.cdc.gov/coronavirus/2019-ncov/hcp/respirator-use-faq.html (Apr. 9, 2021) (6 pages).
Chang et al., Biodegradable electronic systems in 3D, heterogeneously integrated formats. Adv. Mater. 30, 1704955 (2018).
Chatterjee, A.; et al., In vitro and in vivo comparison of dermal irritancy of jet fuel exposure using EpiDerm™(EPI-200) cultured human skin and hairless rats. Toxicology letters 2006, 167, (2), 85-94.
Chen, C.-C.; et al. Aerosol Penetration through Surgical Masks. American journal of infection control 1992, 20 (4), 177-184.
Chen, M.-C. et al. Implantable polymeric microneedles with phototriggerable properties as a patient-controlled transdermal analgesia system. Journal of Materials Chemistry B 2017, 5, (3), 496-503.
Cheng, Y.; et al. Face Masks Effectively Limit the Probability of Sars-Cov-2 Transmission. Science 2021 1439-1443.
Choi, S.; et al. Biodegradable, Efficient, and Breathable Multi-Use Face Mask Filter. Advanced Science 2021, 8 (6), 2003155.
Chorsi MT, et al. Piezoelectric Biomaterials for Sensors and Actuators. Advanced Materials. 2019;31(1):1802084.
Chu et al., "Piezoelectric stimulation by ultrasound facilitates chondrogenesis of mesenchymal stem cells", J Acoustical Society of American, 2020, vol. 148, No. 1, pp. EL58-EL64.
Chu, D. K.; et al. Physical Distancing, Face Masks, and Eye Protection to Prevent Person-to-Person Transmission of Sars-Cov-2 and Covid-19: A Systematic Review and Meta-Analysis. The lancet 2020, 395 (10242), 1973-1987.
Chu, J.; et al. Thinking Green: Modelling Respirator Reuse Strategies to Reduce Cost and Waste. BMJ open 2021, 11 (7), e048687.
Clearfield, D. S., et al. Osteochondral Differentiation of Fluorescent Multireporter Cells on Zonally-Organized Biomaterials. Tissue Engineering Part A 25, 468-486 (2019).

(56) References Cited

OTHER PUBLICATIONS

Cohen, A. J.; et al. Estimates and 25-Year Trends of the Global Burden of Disease Attributable to Ambient Air Pollution: An Analysis of Data from the Global Burden of Diseases Study 2015. The Lancet 2017, 389 (10082), 1907-1918.

Combe, R.; et al. The monosodium iodoacetate model of osteoarthritis: a model of chronic nociceptive pain in rats? Neuroscience letters 2004, 370, (2-3), 236-240.

Cooper MA, et al. Fix the antibiotics pipeline. Nature. 2011;472(7341):32-32.

Creech et al., "Prevention of Recurrent Staphylococcal Skin Infections," Infect Dis Clin North Am. Sep. 2015; 29(3): 429-464.

Crofford, L. J., Use of NSAIDs in treating patients with arthritis. Arthritis research & therapy 2013, 15, (3), S2 (10 pages).

Crone S, et al. A novel in vitro wound biofilm model used to evaluate low-frequency ultrasonic-assisted wound debridement. J Wound Care. 2015;24(2):64-72.

Cui, et al. Study on a piezoelectric micropump for the controlled drug delivery system. Microfluid. Nanofluidics 3, 377-390 (2007).

Curdy, C. et al. Piroxicam delivery into human stratum corneum in vivo: iontophoresis versus passive diffusion. Journal of Controlled Release 2001, 76, (1-2), 73-79.

Curry EJ, et al. Biodegradable nanofiber-based piezoelectric transducer. Proceedings of the National Academy of Sciences. 2020;117(1):214-220.

Curry, E. J.; et al. 3D nano- and micro-patterning of biomaterials for controlled drug delivery. Therapeutic Delivery 2016.

Da Silva et al., Biocompatibility, biodegradation and excretion of polylactic acid (PLA) in medical implants and theranostic systems. Chem. Eng. J. 340, 9-14 (2018).

Daeschlein G, et al. Antibacterial activity of positive and negative polarity low-voltage pulsed current (LVPC) on six typical Gram-positive and Gram-negative bacterial pathogens of chronic wounds. Wound Repair Regen. 2007;15(3):399-403.

Dagdeviren C, et al. Conformable amplified lead zirconate titanate sensors with enhanced piezoelectric response for cutaneous pressure monitoring. Nature Communications. 2014;5(1):4496.

Dagdeviren C, et al. Conformal piezoelectric energy harvesting and storage from motions of the heart, lung, and diaphragm. Proceedings of the National Academy of Sciences. 2014;111(5):1927.

Das, R. et al. Biodegradable Nanofiber Bone-Tissue Scaffold as Remotely-Controlled and Self-Powering Electrical Stimulator. Nano Energy 2020, 105028.

Davidson, C. I.; et al. Airborne Particulate Matter and Human Health: A Review. Aerosol Science and Technology 2005, 39 (8), 737-749.

Degenhart et al., Histological evaluation of a chronically-implanted electrocorticographic electrode grid in a non-human primate. 13, 046019 (2016).

Deleo et al., "Reemergence of antibiotic-resistant *Staphylococcus aureus* in the genomics era," JCL, 2009, 119, 2464-2474.

Deleo FR, Diep BA, Otto M: Host defense and pathogenesis in *Staphylococcus aureus* infections. Infect Dis Clin North Am 2009, 23(1):17-34.

Derakhshandeh H, et al. A Wirelessly Controlled Smart Bandage with 3D-Printed Miniaturized Needle Arrays. Adv Funct Mater. 2020;30(13):1905544.

Desai, T. A.; et al., Nanoporous implants for controlled drug delivery. In BioMEMS and Biomedical Nanotechnology, Springer: 2006; pp. 263-286.

Dimitroulas, T.; et al. In Biologic drugs as analgesics for the management of osteoarthritis, Seminars in arthritis and rheumatism, 2017; Elsevier: pp. 687-691.

Dixon, W. J. et al. A method for obtaining and analyzing sensitivity data. Journal of the American Statistical Association 1948, 43, (241), 109-126.

Dominguez, C. A. et al. Sex differences in the development of localized and spread mechanical hypersensitivity in rats after injury to the infraorbital or sciatic nerves to create a model for neuropathic pain. Gender medicine 2009, 6, 225-234.

Dong P-T, et al. Photolysis of Staphyloxanthin in Methicillin-Resistant *Staphylococcus aureus* Potentiates Killing by Reactive Oxygen Species. Advanced Science. 2019;6(11):1900030.

Donnelly, R. F.; et al. Hydrogel-forming microneedle arrays for enhanced transdermal drug delivery. Advanced functional materials 2012, 22, (23), 4879-4890.

Draize, J. H. et al. Methods for the study of irritation and toxicity of substances applied topically to the skin and mucous membranes. Journal of pharmacology and Experimental Therapeutics 1944, 82, (3), 377-390.

Dwyer DJ, et al. Antibiotics induce redox-related physiological alterations as part of their lethality. Proceedings of the National Academy of Sciences of the United States of America. 2014;111(20):E2100-2109.

Englander L, et al. Nitric oxide nanoparticle technology: a novel antimicrobial agent in the context of current treatment of skin and soft tissue infection. J Clin Aesthet Dermatol. 2010;3(6):45-50.

Eppley BL, et al. Degradation characteristics of PLLA-PGA bone fixation devices. The Journal of craniofacial surgery. 1997;8(2):116-120.

Esposito S, et al. Antimicrobial Treatment of *Staphylococcus aureus* in Patients With Cystic Fibrosis. Front Pharmacol. 2019;10:849-849.

Farah et al. Physical and mechanical properties of PLA, and their functions in widespread applications—a comprehensive review. Adv. Drug Deliv. Rev. 107, 367-392 (2016).

FDA. N95 Respirators, Surgical Masks, and Face Masks. https://www.fda.gov/medical-devices/personal-protective- equipment-infection-control/n95-respirators-surgical-masks-face-masks-and-barrier-face-coverings Last updated Jul. 19, 2022 (6 pages).

Feng, Y. et al. Engineering Spherical Lead Zirconate Titanate to Explore the Essence of Piezo-Catalysis. Nano Energy 2017, 40, 481-486.

Feng, Y.; et al. Self-Powered Electrostatic Filter with Enhanced Photocatalytic Degradation of Formaldehyde Based on Built-in Triboelectric Nanogenerators. ACS nano 2017, 11 (12), 12411-12418.

Formenti, D.; et al. Thermal imaging of exercise-associated skin temperature changes in trained and untrained female subjects. Annals of biomedical engineering 2013, 41, (4), 863-871.

Fosslien, E., Adverse effects of nonsteroidal anti-inflammatory drugs on the gastrointestinal system. Annals of Clinical & Laboratory Science 1998, 28, (2), 67-81.

Foti JJ, et al. Oxidation of the Guanine Nucleotide Pool Underlies Cell Death by Bactericidal Antibiotics. Science. 2012;336(6079):315-319.

Freeman J, et al. Comparison of the efficacy of ramoplanin and vancomycin in both in vitro and in vivo models of clindamycin-induced Clostridium difficile infection. J Antimicrob Chemother. 2005;56(4):717-725.

Friebe, M.; et al. Synovial distribution of "systemically" administered acetylsalicylic acid in the isolated perfused equine distal limb. BMC veterinary research 2013, 9, (1), 56.

Frim, J. et al. Body composition and skin temperature variation. Journal of Applied Physiology 1990, 68, (2), 540- 543.

Fu, C.-H. J. et al. Method for determination of aspirin and salicylic acid in rat whole blood by high pressure liquid chromatography. Analytical Letters 1985, 18, (3), 269-277.

Gabriel D, et al. A photo-triggered layered surface coating producing reactive oxygen species. Biomaterials. 2013;34(38):9763-9769.

Gao, Q., et al. Ultrasound Stimulation of Different Dental Stem Cell Populations: Role of Mitogen-activated Protein Kinase Signaling. J. Endod. 42, 2016, 425-431.

Garland MJ(1), Migalska K, Mahmood TM, Singh TR, Woolfson AD, Donnelly RF. Microneedle arrays as medical devices for enhanced transdermal drug delivery Expert Rev Med Devices. Jul. 2011;8(4):459-82.

Gentile, P. et al. An overview of poly (lactic-co-glycolic) acid (PLGA)-based biomaterials for bone tissue engineering. International journal of molecular sciences 2014, 15, (3), 3640-3659.

Gibaldi, M. et al. Bioavailability of aspirin from commercial suppositories. Journal of pharmaceutical sciences 1975, 64, (6), 1064-1066.

(56) References Cited

OTHER PUBLICATIONS

Gohil, S. V. et al. Spatially controlled rhBMP-2 mediated calvarial bone formation in a transgenic mouse model. International journal of biological macromolecules 2018, 106, 1159-1165.

Golabchi et al., Melatonin improves quality and longevity of chronic neural recording. 180, 225-239 (2018).

Gordon CP, Williams P, Chan WC: Attenuating *Staphylococcus aureus* virulence gene regulation: a medicinal chemistry perspective. J Med Chem 2013, 56(4):1389-1404.

Gottlieb, H. E.; et al. NMR Chemical Shifts of Common Laboratory Solvents as Trace Impurities. Journal of Organic Chemistry 1997, 62 (21), 7512-7515.

Grant SS, et al. Eradication of bacterial persisters with antibiotic-generated hydroxyl radicals. Proceedings of the National Academy of Sciences. 2012; 109(30):12147.

Grassi, M.; et al. Mathematical modelling and controlled drug delivery: matrix systems. Current drug delivery 2005, 2, (1), 97-116.

Gu, G. Q. et al. Triboelectric Nanogenerator Enhanced Nanofiber Air Filters for Efficient Particulate Matter Removal. ACS Nano 2017, 11 (6), 6211-6217.

Guerin et al., Control of piezoelectricity in amino acids by supramolecular packing. Nat. Mater. 17, 180-186 (2018).

Guo, H.; et al. A pure zinc membrane with degradability and osteogenesis promotion for guided bone regeneration: in vitro and in vivo studies. Acta Biomater. 2020, 396-409.

Gurung, D. et al. Transient temperature distribution in human dermal part with protective layer at low atmospheric temperature. International Journal of Biomathematics 2010, 3, (04), 439-451.

Gustafsson, M. et al. Pain, coping and analgesic medication usage in rheumatoid arthritis patients. Patient education and counseling 1999, 37, (1), 33-41.

Gutarowska, B., et al. "PLA nonwovens modified with poly (dimethylaminoethyl methacrylate) as antimicrobial filter materials for workplaces." Textile Research Journal 85.10 (2015): 1083-1094.

Haddadin et al., "Methicillin resistant *Staphylococcus aureus* (MRSA) in the intensive care unit," Postgraduate Medical Journal 2002; 78:385-392.

Hasuike A, et al. In vivo bone regenerative effect of low-intensity pulsed ultrasound in rat calvarial defects. Oral Surgery, Oral Medicine, Oral Pathology, Oral Radiology, and Endodontology. 2011;111(1):e12-e20.

Hauert AB, Martinelli S, Marone C, Niggli V: Differentiated HL-60 cells are a valid model system for the analysis of human neutrophil migration and chemotaxis. Int J Biochem Cell Biol 2002, 34(7):838-854.

He, M. et al. Intradermal implantable PLGA microneedles for etonogestrel sustained release. Journal of Pharmaceutical Sciences 2020, 1958-1966.

He, Z. et al. An overview of hydrogel-based intra-articular drug delivery for the treatment of osteoarthritis. Colloids and Surfaces B: Biointerfaces 2017, 154, 33-39.

Hickey, D.J., et al. Electrophoretic deposition of MgO nanoparticles imparts antibacterial properties to poly-L- lactic acid for orthopedic applications. Journal of Biomedical Materials Research Part A, 2017, 105(11), 3136-3147.

Hong K-S, et al. Piezoelectrochemical Effect: A New Mechanism for Azo Dye Decolorization in Aqueous Solution through Vibrating Piezoelectric Microfibers. The Journal of Physical Chemistry C. 2012;116(24):13045-13051.

Horodyckid et al., Safe long-term repeated disruption of the blood-brain barrier using an implantable ultrasound device: A multiparametric study in a primate model. J. Neurosurg. 126, 1351-1361 (2017).

Hossain, E.; et al. Recharging and Rejuvenation of Decontaminated N95 Masks. Physics of Fluids 2020, 32 (9), 093304.

Howard, J.; et al., An Evidence Review of Face Masks against Covid-19. Proceedings of the National Academy of Sciences 2021, 118 (4).

Hu H, et al. Stretchable ultrasonic transducer arrays for three-dimensional imaging on complex surfaces. Science Advances. 2018;4(3):eaar3979.

Huang, X.; et al. On the importance and mechanisms of burst release in matrix-controlled drug delivery systems. Journal of controlled release 2001, 73, (2-3), 121-136.

Hui J, et al. Photo-Disassembly of Membrane Microdomains Revives Conventional Antibiotics against MRSA. Advanced Science. 2020;7(6):1903117.

Iati, M. More Experts Now Recommend Medical Masks. Good Ones Are Hard to Find. Feb. 2, 2021. https://www.washingtonpost.com/health/2021/02/02/medical-mask-shortage/ (4 pages).

IDATA Reasearch. 2017 US Dental Barrier Membrane Market Driven by Increased Use of Resorbable Membranes. https://idataresearch.com/2017-us-dental-barrier-membrane-market-driven-increased-use-resorbable-membranes/. Nov. 10, 2017. (6 pages).

Idbaih et al., Safety and feasibility of repeated and transient blood-brain barrier disruption by pulsed ultrasound in patients with recurrent glioblastoma. Clin. Cancer Res. 25, 3793-3801 (2019).

Ikada et al. Enhancement of bone formation by drawn poly(L-lactide). J. Biomed. Mater. Res. 30, 553-558 (1996).

Indian Office Action for Application 202037042930 dated Jun. 20, 2022 (6 pages).

Infection Control Today, "New Research Estimates MRSA Infections Cost U.S. Hospitals $3.2 Billion to $4.2 Billion Annually," <https://www.infectioncontroltoday.com/view/new-research-estimates-mrsa-infections-cost-US-hospitals-32-billion-42-billion-annually> dated May 16, 2005.

Institute of Medicine of the National Academies. Characteristics of Respirators and Medical Masks. In Reusability of Facemasks During an Influenza Pandemic: Facing the Flu, 2006; pp. 22-42.

International Preliminary Report on Patentability for Application No. PCT/US2021/021677 dated Sep. 6, 2022 (11 pages).

International Search Report and Written Opinion for Application No. PCT/US21/53887 dated Jan. 28, 2022 (14 pages).

Jacobi, U. et al. Porcine ear skin: an in vitro model for human skin. Skin Research and Technology 2007, 13, (1), 19-24.

Ji, W. et al. Incorporation of stromal cell-derived factor-1α in PCL/gelatin electrospun membranes for guided bone regeneration. Biomaterials 34, 735-745 (2013).

Jin Y, Li M, Shang Y, Liu L, Shen X, Lv Z, Hao Z, Duan J, Wu Y, Chen C et al: Sub-Inhibitory Concentrations of Mupirocin Strongly Inhibit Alpha-Toxin Production in High-Level Mupirocin-Resistant MRSA by Down-Regulating agr, saeRS, and sarA. Front Microbiol 2018, 9:993.

Jung, Y.-s. et al. Thermo-sensitive injectable hydrogel based on the physical mixing of hyaluronic acid and Pluronic F-127 for sustained NSAID delivery. Carbohydrate polymers 2017, 156, 403-408.

Jüni, P.; et al. Intra-articular corticosteroid for knee osteoarthritis. Cochrane Database of Systematic Reviews 2015, (10) (81 pages).

Kalali Y, Haghighat S, Mahdavi M: Passive immunotherapy with specific IgG fraction against autolysin: Analogous protectivity in the MRSA infection with antibiotic therapy. Immunol Lett 2019, 212:125-131.

Kaushik, S. et al. Lack of pain associated with microfabricated microneedles. Anesthesia & Analgesia 2001, 92, (2), 502-504.

Kean, T.; et al. Biodegradation, Biodistribution and Toxicity of Chitosan. Advanced drug delivery reviews 2010, 62 (1), 3-11.

Kern, H., et al. Recovery of long-term denervated human muscles induced by electrical stimulation. Muscle & nerve 31, 98-101 (2005).

Khalid, B.; et al., Direct Blow-Spinning of Nanofibers on a Window Screen for Highly Efficient Pm2. 5 Removal. Nano letters 2017, 17 (2), 1140-1148.

Khanal, M.; et al. Injectable nanocomposite analgesic delivery system for musculoskeletal pain management. Acta biomaterialia 2018, 74, 280-290.

Kim, D.-H. et al. Sustained release of dexamethasone from hydrophilic matrices using PLGA nanoparticles for neural drug delivery. Biomaterials 2006, 27, (15), 3031-3037.

Kinoshita, N. et al. Noninvasive localized delivery of Herceptin to the mouse brain by MRI-guided focused ultrasound-induced bloodbrain barrier disruption. Proc. Natl. Acad. Sci. U.S.A. 103, 11719-11723 (2006).

Klein et al., "National Costs Associated With Methicillin-Susceptible and Methicillin-Resistant *Staphylococcus aureus* Hos-

(56) References Cited

OTHER PUBLICATIONS pitalizations in the United States, 2010-2014," Clinical Infectious Diseases, vol. 68, Issue 1, Jan. 1, 2019, pp. 22-28.
Kloth, L. C. Electrical stimulation for wound healing: a review of evidence from in vitro studies, animal experiments, and clinical trials. The international journal of lower extremity wounds 4, 23-44 (2005).
Kobayashi, et al. Label-free imaging of melanoma with confocal photothermal microscopy: Differentiation between malignant and benign tissue. Bioeng. 5, 67 (2018) (18 pages).
Kohanski MA, et al. A Common Mechanism of Cellular Death Induced by Bactericidal Antibiotics. Cell. 2007;130(5):797-810.
Kozai et al., Chronic tissue response to carboxymethyl cellulose based dissolvable insertion needle for ultra-small neural probes. 35, 9255-9268 (2014).
Krasowska A, et al. How microorganisms use hydrophobicity and what does this mean for human needs? Front Cell Infect Microbiol. 2014;4:112-112.
Kullenberg, B. et al. Intraarticular corticosteroid injection: pain relief in osteoarthritis of the hip? The Journal of rheumatology 2004, 31, (11), 2265-2268.
Latimer, J. M. et al. Microwave Oven Irradiation as a Method for Bacterial Decontamination in a Clinical Microbiology Laboratory. Journal of Clinical Microbiology 1977, 6 (4), 340-342.
Laurencin, C. T.; et al. Delivery of small molecules for bone regenerative engineering: preclinical studies and potential clinical applications. Drug discovery today 2014, 19, (6), 794-800.
Lausen M, Pedersen MS, Rahman NSK, Holm-Nielsen LT, Farah FYM, Christiansen G, Birkelund S: Opsonophagocytosis of Chlamydia pneumoniae by Human Monocytes and Neutrophils. Infect Immun 2020, 88(7).
Leatherby, L. As Covid Cases Rise All over U.S., Lower Vaccination Rates Point to Worse Outcomes. Jul. 31, 2021. https://www.nytimes.com/interactive/2021/07/31/us/covid-delta-cases-deaths.html?action=click&module=Spotlight&pgtype=Homepage (3 pages).
Lee et al., Lactic acid assisted fabrication of bioactive three-dimensional PLLA/β-TCP fibrous scaffold for biomedical application. Chem. Eng. J. 347, 771-781 (2018).
Lee, et al. Piezoelectric properties of electrospun poly(L-lactic acid) nanofiber web. Mater. Lett. 148, 58-62 (2015).
Leung, L. et al. Comparison of morphology and mechanical properties of PLGA bioscaffolds. Biomedical Materials 2008, 3, (2), 025006.
Lewin et al., Free serum haemoglobin is associated with brain atrophy in secondary progressive multiple sclerosis. Wellcome Open Res. 1, 10 (2016) (23 pages).
Lewitus, S. et al. The Effect of Nanoclays on the Properties of PLLA-modified Polymers Part 1: Mechanical and Thermal Properties. Journal of Polymers and the Environment 14, 171-177 (2006).
Li J, et al. Evaluation of Ultrasound-Induced Damage to *Escherichia coli* and *Staphylococcus aureus* by Flow Cytometry and Transmission Electron Microscopy. Appl Environ Microbiol. 2016;82(6):1828-1837.
Li Z, et al. Using Positively Charged Magnetic Nanoparticles to Capture Bacteria at Ultralow Concentration. Nanoscale Research Letters. 2019;14(1):195 (8 pages).
Li, C. et al. Dual-mode operation of flexible piezoelectric polymer diaphragm for intracranial pressure measurement. Appl. Phys. Lett. 96, 053502 (2010).
Li, H. et al. Enhancing the Mechanical Properties of Electrospun Nanofiber Mats through Controllable Welding at the Cross Points. Macromolecular rapid communications 2017, 38 (9), 1600723.
Li, N.; et al. A Work Group Report on Ultrafine Particles (American Academy of Allergy, Asthma & Immunology): Why Ambient Ultrafine and Engineered Nanoparticles Should Receive Special Attention for Possible Adverse Health Outcomes in Human Subjects. Journal of Allergy and Clinical Immunology 2016, 138 (2), 386-396.
Li, P. et al. Air Filtration in the Free Molecular Flow Regime: A Review of High-Efficiency Particulate Air Filters Based on Carbon Nanotubes. Small 2014, 10 (22), 4543-4561.
Li, P. et al. Apatite formation induced by silica gel in a simulated body fluid. Journal of the American Ceramic Society 1992, 75, (8), 2094-2097.
Li, Q. et al. Involvement of the spinal NALP1 inflammasome in neuropathic pain and aspirin-triggered-15-epi-lipoxin A4 induced analgesia. Neuroscience 2013, 254, 230-240.
Li, W. et al. Rapidly separable microneedle patch for the sustained release of a contraceptive. Nature Biomedical Engineering 2019, 3, (3), 220-229.
Li, W.; et al. Long-acting reversible contraception by effervescent microneedle patch. Science advances 2019, 5, (11), eaaw8145.
Liao, L.; et al. Can N95 Respirators Be Reused after Disinfection? How Many Times? ACS nano 2020, 14 (5), 6348-6356.
Liu, C.; et al. Transparent Air Filter for High-Efficiency Pm 2.5 Capture. Nature communications 2015, 6 (1), 1-9.
Liu, G. et al. Self-Powered Electrostatic Adsorption Face Mask Based on a Triboelectric Nanogenerator. ACS applied materials & interfaces 2018, 10 (8), 7126-7133.
Liu, H. et al. High-Performance Pm0. 3 Air Filters Using Self-Polarized Electret Nanofiber/Nets. Advanced Functional Materials 2020, 30 (13), 1909554.
Liu, X. et al. A biodegradable multifunctional nanofibrous membrane for periodontal tissue regeneration. Acta Biomater. 2020, 108, 207-222.
Liu, Z.; et al. Understanding the Factors Involved in Determining the Bioburdens of Surgical Masks. Annals of translational medicine 2019, 7 (23).
Lo, K. et al. Small-molecule based musculoskeletal regenerative engineering. Trends in biotechnology 2014, 32, (2), 74-81.
Lobritz MA, et al. Antibiotic efficacy is linked to bacterial cellular respiration. Proceedings of the National Academy of Sciences of the United States of America. 2015;112(27):8173-8180.
Lokuta MA, Nuzzi PA, Huttenlocher A: Analysis of neutrophil polarization and chemotaxis. Methods Mol Biol 2007, 412:211-229.
Long Y, et al. Effective Wound Healing Enabled by Discrete Alternative Electric Fields from Wearable Nanogenerators. ACS Nano. 2018;12(12):12533-12540.
Lops, C.; et al. Sonophotocatalytic Degradation Mechanisms of Rhodamine B Dye Via Radicals Generation by Micro-and Nano-Particles of Zno. Applied Catalysis B: Environmental 2019, 243, 629-640.
Lu, W.-C. et al. Effect of magnesium on the osteogenesis of normal human osteoblasts. Magnes. Res. 30, 42-52 (2017).
Lu, X.; et al. Theoretical analysis of calcium phosphate precipitation in simulated body fluid. Biomaterials 2005, 26, (10), 1097-1108.
Ludwig, The velocity of sound through tissues and the acoustic impedance of tissues. The journal of the acoustical society of America 22, 862-866 (1950).
Lundgren, D., et al. "The use of a new bioresorbable barrier for guided bone regeneration in connection with implant installation. Case reports." Clinical Oral Implants Research 5.3 (1994): 177-184.
Luque-Agudo V, et al. Aging of Solvent-Casting PLA-Mg Hydrophobic Films: Impact on Bacterial Adhesion and Viability. Coatings. 2019;9(12) 814.
Luzuriaga MA(1), Berry DR, Reagan JC, Smaldone RA, Gassensmith JJ. Biodegradable 3D printed polymer microneedles for transdermal drug delivery. Lab Chip. Apr. 17, 2018;18(8):1223-1230.
Lv, D.; et al. Ecofriendly Electrospun Membranes Loaded with Visible-Light-Responding Nanoparticles for Multifunctional Usages: Highly Efficient Air Filtration, Dye Scavenging, and Bactericidal Activity. ACS applied materials & interfaces 2019, 11 (13), 12880-12889.
Mahdavi, A. et al. Particle Loading Time and Humidity Effects on the Efficiency of an N95 Filtering Facepiece Respirator Model under Constant and Inhalation Cyclic Flows. Annals of Occupational Hygiene 2015, 59 (5), 629-640.
Manoukian, M. A. C. et al. Topical administration of ibuprofen for injured athletes: considerations, formulations, and comparison to oral delivery. Sports medicine-open 2017, 3, (1), 36, 1-9.

(56) References Cited

OTHER PUBLICATIONS

Marzoli, F. et al. Long-lasting, antinociceptive effects of pH-sensitive niosomes loaded with ibuprofen in acute and chronic models of pain. Pharmaceutics 2019, 11, (2), 62, 1-12.
McAllister DV(1), Wang PM, Davis SP, Park JH, Canatella PJ, Allen MG, Prausnitz MR. Microfabricated needles for transdermal delivery of macromolecules and nanoparticles: fabrication methods and transport studies. Proc Natl Acad Sci U S A. Nov. 25, 2003;100(24):13755-60.
McCrudden, M. T et al. Design and physicochemical characterisation of novel dissolving polymeric microneedle arrays for transdermal delivery of high dose, low molecular weight drugs. Journal of Controlled Release 2014, 180, 71-80.
McDannold, et al. MRI-guided targeted blood-brain barrier disruption with focused ultrasound: Histological findings in rabbits. Ultrasound Med. Biol. 31, 1527-1537 (2005).
Meylan S, et al. Targeting Antibiotic Tolerance, Pathogen by Pathogen. Cell. 2018;172(6):1228-1238.
Middleton, J. C.; Tipton, A. J., Synthetic Biodegradable Polymers as Orthopedic Devices. Biomaterials 2000, 21 (23), 2335-2346.
Mihai MM, et al. Nanomaterials for Wound Healing and Infection Control. Materials (Basel). 2019; 12(13):2176.
Millius A, Weiner OD: Chemotaxis in neutrophil-like HL-60 cells. Methods Mol Biol 2009, 571:167-177.
Moga, K. A. et al. Rapidly-dissolvable microneedle patches via a highly scalable and reproducible soft lithography approach. Advanced Materials 2013, 25, (36), 5060-5066.
Mohseni et al., "Gellan gel comprising short PVDF based-nanofibers: The effect of piezoelectric nanofiber on the mechanical and electrical behavior," Materialstoday Communications, vol. 26, Mar. 2021, 101785.
Monsen T, et al. In Vitro Effect of Ultrasound on Bacteria and Suggested Protocol for Sonication and Diagnosis of Prosthetic Infections. J Clin Microbiol. 2009;47(8):2496-2501.
Montgomery CP, Boyle-Vavra S, Daum RS: Importance of the global regulators Agr and SaeRS in the pathogenesis of CA-MRSA USA300 infection. PLOS One 2010, 5(12):e15177.
Morel CM, et al. Stoking the antibiotic pipeline. BMJ. 2010;340:1115-1118.
Nair, L. S.; et al. Polymers as biomaterials for tissue engineering and controlled drug delivery. In Tissue engineering I, Springer: 2005; pp. 47-90.
Najdovski, L. et al. The Killing Activity of Microwaves on Some Non-Sporogenic and Sporogenic Medically Important Bacterial Strains. Journal of Hospital Infection 1991, 19 (4), 239-247.
Nasajpour, A. et al. A multifunctional polymeric periodontal membrane with osteogenic and antibacterial characteristics. Adv. Funct. Mater. 28, 1703437 (2018).
Nazir, M. A. Prevalence of periodontal disease, its association with systemic diseases and prevention. International journal of health sciences 11, 72 (2017), 72-80.
Neely RM, et al. Recent advances in neural dust: towards a neural interface platform. Current Opinion in Neurobiology. 2018;50:64-71.
Nguyen, "A novel injectable piezoelectric hydrogel for osteoarthritis treatment," NIH Project No. 1R21AR074645-01, Award notice date: Apr. 23, 2019, Project Start Date: Jun. 1, 2019 <https://reporter.nih.gov/project-details/9651964> (3 pages).
Nicosia, A., et al. "Air filtration and antimicrobial capabilities of electrospun PLA/PHB containing ionic liquid." Separation and Purification Technology 154 (2015): 154-160.
Nielsen A, Mansson M, Bojer MS, Gram L, Larsen TO, Novick RP, Frees D, Frokiaer H, Ingmer H: Solonamide B inhibits quorum sensing and reduces Staphylococcus aureus mediated killing of human neutrophils. PLOS One 2014, 9(1):e84992.
Noguchi, Y. Why N95 Masks Are Stil in Short Supply in the U.S. https://www.npr.org/sections/health-shots/2021/01/27/960336778/why-n95-masks-are-still-inshort-supply-in-the-u-s, Jan. 27, 2021 (17 pages).
Norman, J. J.; et al. Microneedle patches: usability and acceptability for self-vaccination against influenza. Vaccine 2014, 32, (16), 1856-1862.
Novotny et al. Molybdenum intake influences molybdenum kinetics in men. J. Nutr. 137, 37-42 (2007).
O'Dowd et al., "Face Masks and Respirators in the Fight Against the COVID-19 Pandemic: A Review of Current Materials, Advances and Future Perspectives," Materials 2020, 13(15), 3363.
Olatunji, O.; et al. Microneedle-assisted transdermal delivery of acetylsalicylic acid (aspirin) from biopolymer films extracted from fish scales. Polymer Bulletin 2018, 75, (9), 4103-4115.
Omidinia-Anarkoli, A.; et al. An Injectable Hybrid Hydrogel with Oriented Short Fibers Induces Unidirectional Growth of Functional Nerve Cells. Small 2017, 13, (36).
O'Riordan K, Lee JC: Staphylococcus aureus capsular polysaccharides. Clin Microbiol Rev 2004, 17(1):218-234.
Padilla F, et al. Stimulation of bone repair with ultrasound: A review of the possible mechanic effects. Ultrasonics. 2014;54(5):1125-1145.
Panieri E, et al. ROS signaling and redox biology in endothelial cells. Cell Mol Life Sci. 2015;72(17):3281-3303.
Pankey GA, et al. Clinical relevance of bacteriostatic versus bactericidal mechanisms of action in the treatment of Gram-positive bacterial infections. Clin Infect Dis. 2004;38(6):864-870.
Park, J.-H. et al. Biodegradable polymer microneedles: fabrication, mechanics and transdermal drug delivery. Journal of controlled release 2005, 104, (1), 51-66.
Parlet CP, Kavanaugh JS, Crosby HA, Raja HA, El-Elimat T, Todd DA, Pearce CJ, Cech NB, Oberlies NH, Horswill AR: Apicidin Attenuates MRSA Virulence through Quorum-Sensing Inhibition and Enhanced Host Defense. Cell Rep 2019, 27(1):187-198 e186.
Patel et al., "Development of a Sonically Powered Biodegradable Nanogenerator for Bone Regeneration", 2019, University of Connecticut, 46 pages.
Pathak, R. K. et al. A nanoparticle cocktail: temporal release of predefined drug combinations. Journal of the American Chemical Society 2015, 137, (26), 8324-8327.
Patrick, J.; et al. A randomized trial to assess the pharmacodynamics and pharmacokinetics of a single dose of an extended-release aspirin formulation. Postgraduate medicine 2015, 127, (6), 573-580.
Paul, et al. Novel 3D analysis of Claudin-5 reveals significant endothelial heterogeneity among CNS microvessels. 86, 1-10 (2013).
Pavel A, et al. Prophylactic Antibiotics in Clean Orthopaedic Surgery. JBJS. 1974;56(4):777-782.
Pelletier, J.-P.; et al. In Efficacy and safety of oral NSAIDs and analgesics in the management of osteoarthritis: Evidence from real-life setting trials and surveys, Seminars in arthritis and rheumatism, 2016; Elsevier: pp. S22-S27.
Peltoniemi et al. SR-PLLA and SRPGA miniscrews: Biodegradation and tissue reactions in the calvarium and dura mater. J. Craniomaxillofac. Surg. 27, 42-50 (1999).
Peng, X., et al. "A breathable, biodegradable, antibacterial, and self-powered electronic skin based on all-nanofiber triboelectric nanogenerators." Science Advances 6.26 (2020): eaba9624.
Peterson RV, et al. The effect of frequency and power density on the ultrasonically-enhanced killing of biofilm-sequestered Escherichia coli. Colloids and Surfaces B: Biointerfaces. 2000;17(4):219-227.
Prausnitz, M. R. Engineering microneedle patches for vaccination and drug delivery to skin. Annual review of chemical and biomolecular engineering 2017, 8, 177-200.
Pressmeddelande, "Microneedle Drug Delivery Systems Market 2018 Segmentation, Demand, Growth, Trend, Opportunity and Forecast to 2023," My News Desk, <https://www.mynewsdesk.com/se/probe-way/pressreleases/microneedle-drug-delivery-systems-market-2018-segmentation-demand-growth-trend-opportunity-and-forecast-to-2023-2672909> dated Sep. 3, 2018.
Prokusil. Prophylactic Antibiotics in Orthopaedic Surgery. JAAOS—Journal of the American Academy of Orthopaedic Surgeons. 2008; 16(5):283-293.
Qian, Y. et al. Performance of N95 Respirators: Filtration Efficiency for Airborne Microbial and Inert Particles. American Industrial Hygiene Association Journal 1998, 59 (2), 128-132.

(56) References Cited

OTHER PUBLICATIONS

Qiu, Y. et al. Enhancement of skin permeation of docetaxel: a novel approach combining microneedle and elastic liposomes. Journal of Controlled Release 2008, 129, (2), 144-150.

Queck SY, Jameson-Lee M, Villaruz AE, Bach TH, Khan BA, Sturdevant DE, Ricklefs SM, Li M, Otto M: RNAIII-independent target gene control by the agr quorum-sensing system: insight into the evolution of virulence regulation in *Staphylococcus aureus*. Mol Cell 2008, 32(1):150-158.

Quinn, H. L. et al. Design of a dissolving microneedle platform for transdermal delivery of a fixed-dose combination of cardiovascular drugs. Journal of pharmaceutical sciences 2015, 104, (10), 3490-3500.

Ratajska, M. et al. Studies on the Biodegradation of Chitosan in an Aqueous Medium. Fibres & Textiles in Eastern Europe 2003, (3 (42)), 75--79.

Raynor, P. C. et al. The Long-Term Performance of Electrically Charged Filters in a Ventilation System. Journal of occupational and environmental hygiene 2004, 1 (7), 463-471.

Resistance Who-TICGIoA: No time to wait: Securing the future from drug-resistant infections. In.; 2019. 28 pages.

Rigby KM, DeLeo FR: Neutrophils in innate host defense against *Staphylococcus aureus* infections. Semin Immunopathol 2012, 34(2):237-259.

Riggin, C. N.; et al. Intra-articular tibiofemoral injection of a nonsteroidal anti-inflammatory drug has No. detrimental effects on joint mechanics in a rat model. Journal of Orthopaedic Research 2014, 32, (11), 1512-1519.

Ripolin, A.; et al. Successful application of large microneedle patches by human volunteers. International journal of pharmaceutics 2017, 521, (1-2), 92-101.

Rizzello L, et al. Nanotechnology tools for antibacterial materials. Nanomedicine (Lond). 2013;8(5):807-821.

Roberts, M. S. et al. Percutaneous absorption of topically applied NSAIDS and other compounds: role of solute properties, skin physiology and delivery systems. Inflammopharmacology 1999, 7, (4), 339.

Robertson JMC, et al. A comparison of the effectiveness of TiO2 photocatalysis and UVA photolysis for the destruction of three pathogenic micro-organisms. Journal of Photochemistry and Photobiology A: Chemistry. 2005;175(1):51-56.

Rohrer, M. D. et al. Microwave Sterilization. Journal of the American Dental Association (1939) 1985, 110 (2), 194-198.

Roy S, et al. Disposable Patterned Electroceutical Dressing (PED-10) Is Safe for Treatment of Open Clinical Chronic Wounds. Advances in Wound Care. 2019;8(4):149-159.

Runyan CM, et al. Low-frequency ultrasound increases outer membrane permeability of Pseudomonas aeruginosa. The Journal of General and Applied Microbiology. 2006;52(5):295-301.

Ruparelia JP, et al. Strain specificity in antimicrobial activity of silver and copper nanoparticles. Acta Biomater. 2008;4(3):707-716.

Russell, R., Non-steroidal anti-inflammatory drugs and gastrointestinal damage—problems and solutions. Postgraduate medical journal 2001, 77, (904), 82-88.

Sadorsky, P., The Effect of Urbanization and Industrialization on Energy Use in Emerging Economies: Implications for Sustainable Development. American Journal of Economics and Sociology 2014, 73 (2), 392-409.

Salomoni R, et al. Antibacterial effect of silver nanoparticles in Pseudomonas aeruginosa. Nanotechnol Sci Appl. 2017;10:115-121.

Santora, M. et al. Covid Updates: Known Global Tool Reaches 200 Millions Virus Infections. Aug. 4, 2021. https://web.archive.org/web/20210804234532/https://www.nytimes.com/live/2021/08/04/world/covid-delta-variant-vaccine (21 pages).

Schlesinger, E. et al. Polycaprolactone thin-film drug delivery systems: empirical and predictive models for device design. Materials Science and Engineering: C 2015, 57, 232-239.

Schlesinger, E.; et al. A tunable, biodegradable, thin-film polymer device as a long-acting implant delivering tenofovir alafenamide fumarate for HIV pre-exposure prophylaxis. Pharmaceutical research 2016, 33, (7), 1649-1656.

Schmook, F. P.; et al. Comparison of human skin or epidermis models with human and animal skin in in-vitro percutaneous absorption. International journal of pharmaceutics 2001, 215, (1-2), 51-56.

Schutze GE, Hall MA, Baker CJ, Edwards MS: Role of neutrophil receptors in opsonophagocytosis of coagulase-negative staphylococci. Infect Immun 1991, 59(8):2573-2578.

Sencadas et al., Local piezoelectric activity of single poly(L-lactic acid) (PLLA) microfibers. Appl. Phys. A 109, 51-55 (2012).

Seth AK, et al. Noncontact, low-frequency ultrasound as an effective therapy against Pseudomonas aeruginosa-infected biofilm wounds. Wound Repair Regen. 2013;21(2):266-274.

Shah SR, et al. Evolving strategies for preventing biofilm on implantable materials. Materials Today. 2013;16(5):177-182.

Shah, S.; et al. Controversies and advances in non-steroidal anti-inflammatory drug (NSAID) analgesia in chronic pain management. Postgraduate medical journal 2012, 88, (1036), 73-78.

Shalumon KT, et al. Sodium alginate/poly(vinyl alcohol)/nano ZnO composite nanofibers for antibacterial wound dressings. Int J Biol Macromol. 2011;49(3):247-254.

Sheets, D.; et al. An Apparatus for Rapid and Nondestructive Comparison of Masks and Respirators. Review of Scientific Instruments 2020, 91 (11), 114101.

Shim, J.-H. et al. Efficacy of rhBMP-2 loaded PCL/PLGA/β-TCP guided bone regeneration membrane fabricated by 3D printing technology for reconstruction of calvaria defects in rabbit. Biomedical materials 9, 065006 (2014) (9 pages).

Shokri, J.; et al. Swellable elementary osmotic pump (SEOP): an effective device for delivery of poorly water-soluble drugs. European Journal of Pharmaceutics and Biopharmaceutics 2008, 68, (2), 289-297.

Shrivasta VA S, et al. Characterization of enhanced antibacterial effects of novel silver nanoparticles. Nanotechnology. 2007;18(22):225103 (9 pages).

Shuai et al., "Surface modification enhances interfacial bonding in PLLA/MgO bone scaffold," Materials Science and Engineering: C, vol. 108, Mar. 2020, 110486.

Shuai, C. et al. nMgO-incorporated PLLA bone scaffolds: Enhanced crystallinity and neutralized acidic products. Materials & Design 174, 107801 (2019).

Silva, E.; et al. Pdlla Honeycomb-Like Scaffolds with a High Loading of Superhydrophilic Graphene/Multi-Walled Carbon Nanotubes Promote Osteoblast in Vitro Functions and Guided in Vivo Bone Regeneration. Materials Science and Engineering: C 2017, 73, 31-39.

Sinatra, R.S.; et al. Efficacy and safety of single and repeated administration of 1 gram intravenous acetaminophen injection (paracetamol) for pain management after major orthopedic surgery. Anesthesiology: The Journal of the American Society of Anesthesiologists 2005, 102, (4), 822-831.

Smith et al. Direct observation of shear piezoelectricity in poly-L-lactic acid nanowires. APL Mater. 5, 074105 (2017) (8 pages).

Starr MB, et al. Coupling of piezoelectric effect with electrochemical processes. Nano Energy. 2015;14:296-311.

Stokes, A.; et al. The contribution of obesity to prescription opioid use in the United States. Pain 2019, 160, (10), 2255.

Subbiahdoss G, et al. Magnetic targeting of surface-modified superparamagnetic iron oxide nanoparticles yields antibacterial efficacy against biofilms of gentamicin-resistant staphylococci. Acta Biomater. 2012;8(6):2047-2055.

Sultana et al., Human skin interactive self-powered wearable piezoelectric bio-eskin by electrospun poly-L-lactic acid nanofibers for non-invasive physiological signal monitoring. J. Mater. Chem. B 5, 7352-7359 (2017).

Sutton et al., "Hospital-, Health Care-, and Community-Acquired MRSA: Estimates From California Hospitals, 2013," <https://www.hcup-us.ahrq.gov/reports/statbriefs/sb212-MRSA-Hospital-Stays-California-2013.jsp> dated Oct. 2016.

(56) References Cited

OTHER PUBLICATIONS

Szablowski, et al. Acoustically targeted chemogenetics for the non-invasive control of neural circuits. Nat. Biomed. Eng. 2, 475-484 (2018).
Taguchi, V. et al. Determination of drug stability in aspirin tablet formulations by high-pressure liquid chromatography. Journal of pharmaceutical sciences 1981, 70, (1), 64-67.
Tajitsu et al. Novel tweezers for biological cells using piezoelectric polylactic acid fibers. Ferroelectrics 320, 133-139 (2005).
Tajitsu, Y. Fundamental study on improvement of piezoelectricity of poly(ι-lactic acid) and its application to film actuators. IEEE Trans. Ultrason. Ferroelectr. Freq. Control 60, 1625-1629 (2013).
Takeuchi, H.; et al. Influence of skin thickness on the in vitro permeabilities of drugs through Sprague-Dawley rat or Yucatan micropig skin. Biological and Pharmaceutical Bulletin 2012, 35, (2), 192-202.
Tams J, et al. Poly(1-lactide) bone plates and screws for internal fixation of mandibular swing osteotomies. Int J Oral Maxillofac Surg. 1996;25(1):20-24.
Tan, et al. Studies on Thermal Decomposition Mechanism and Kinetics of Aspirin [J]. Acta Physico-chimica Sinica 2004, 1m 50-54. With English Abstract.
Tan, G., et al. "Surface-selective preferential production of reactive oxygen species on piezoelectric ceramics for bacterial killing." ACS applied materials & interfaces 8.37 (2016): 24306-24309.
Tao H, et al. Silk-based resorbable electronic devices for remotely controlled therapy and in vivo infection abatement. Proceedings of the National Academy of Sciences. 2014;111(49):17385.
Tezel A, et al. Topical Delivery of Anti-sense Oligonucleotides Using Low-Frequency Sonophoresis. Pharm Res. 2004;21(12):2219-2225.
Thakur, R. R. S.; et al. Microneedle-mediated intrascleral delivery of in situ forming thermoresponsive implants for sustained ocular drug delivery. Journal of Pharmacy and Pharmacology 2014, 66, (4), 584-595.
Thamma Vongsa V, Kim HK, Missiakas D, Schneewind O: Staphylococcal manipulation of host immune responses. Nat Rev Microbiol 2015, 13(9):529-543.
THERMOFISHER Scientific. Residual Solvent Analysis Information. Jul. 14, 2019. https://web.archive.org/web/20190714025617/https://www.thermofisher.com/us/en/home/industrial/pharma-biopharma/pharma-biopharma-learning-center/pharmaceutical-qa-qc-information/residual-solvent-analysis-information.html (6 pages).
Timin, A. S., et al. "Multifunctional scaffolds with improved antimicrobial properties and osteogenicity based on piezoelectric electrospun fibers decorated with bioactive composite microcapsules." ACS applied materials & interfaces 10.41 (2018): 34849-34868.
Tong SY, Davis JS, Eichenberger E, Holland TL, Fowler VG, Jr.: *Staphylococcus aureus* infections: epidemiology, pathophysiology, clinical manifestations, and management. Clin Microbiol Rev 2015, 28(3):603-661.
Tran, K. T.; et al. Lithography-based methods to manufacture biomaterials at small scales. Journal of Science: Advanced Materials and Devices 2017, 2, (1), 1-14.
Tucho, G. T.; et al., Universal Use of Face Masks and Related Challenges During Covid-19 in Developing Countries. Risk Management and Healthcare Policy 2021, 14, 511.
Ueki, H.; et al. Effectiveness of Face Masks in Preventing Airborne Transmission of Sars-Cov-2. MSphere 2020, 5 (5), e00637-20.
Ummadi, S.; et al. Overview on controlled release dosage form. System 2013, 7, (8), 51-60.
Valentini, R. F., et al. Electrically charged polymeric substrates enhance nerve fibre outgrowth in vitro. Biomaterials 13, 183-190 (1992).
Van Acker H, et al. The Role of Reactive Oxygen Species in Antibiotic-Mediated Killing of Bacteria. Trends in Microbiology. 2017;25(6):456-466.
Varrone JJ, et al. Passive immunization with anti-glucosaminidase monoclonal antibodies protects mice from implant-associated osteomyelitis by mediating opsonophagocytosis of *Staphylococcus aureus* megaclusters. J Orthop Res 2014, 32(10):1389-1396.
Varrone JJ, Li D, Daiss JL, Schwarz EM: Anti-Glucosaminidase Monoclonal Antibodies as a Passive Immunization for Methicillin-Resistant *Staphylococcus aureus* (MRSA) Orthopaedic Infections. Bonekey Osteovision 2011, 8:187-194.
Vykhodtseva, et al. Progress and problems in the application of focused ultrasound for blood-brain barrier disruption. Ultrasonics 48, 279-296 (2008).
Vysakh et al., "A Comparative Analysis of Community Acquired and Hospital Acquired Methicillin Resistant Staphylococcus Aureus," J Clin Diagn Res. Jul. 2013; 7(7):1339-1342.
Walmsley, A. et al. Ultrasound in dentistry. Part 2-periodontology and endodontics. J. Dent. 20, 11-17 (1992).
Walsh C. Molecular mechanisms that confer antibacterial drug resistance. Nature. 2000;406(6797):775-781.
Wang F, Gao W, Thamphiwatana S, Luk BT, Angsantikul P, Zhang Q, Hu CM, Fang RH, Copp JA, Pornpattananangkul D et al: Hydrogel Retaining Toxin-Absorbing Nanosponges for Local Treatment of Methicillin-Resistant *Staphylococcus aureus* Infection. Adv Mater 2015, 27(22):3437-3443.
Wang Y, et al. Piezo-catalysis for nondestructive tooth whitening. Nature Communications. 2020;11(1):1328.
Wang, C. et al. Enhanced cancer immunotherapy by microneedle patch-assisted delivery of anti-PD1 antibody. Nano letters 2016, 16, (4), 2334-2340.
Wang, C. et al. Silk Nanofibers as High Efficient and Lightweight Air Filter. Nano Research 2016, 9 (9), 2590-2597.
Wang, N. et al. Tunable Fabrication of Three-Dimensional Polyamide-66 Nano-Fiber/Nets for High Efficiency Fine Particulate Filtration. Journal of Materials Chemistry 2012, 22 (4), 1445-1452.
Wang, P. et al. Ultrasmall Barium Titanate Nanoparticles for Highly Efficient Hypoxic Tumor Therapy Via Ultrasound Triggered Piezocatalysis and Water Splitting. ACS nano 2021, 11326-11340.
Wang, S. et al. Controlled release of levonorgestrel from biodegradable poly (D, L-lactide-co-glycolide) microspheres: in vitro and in vivo studies. International journal of pharmaceutics 2005, 301, (1-2), 217-225.
Wang, S. et al. Electret Polyvinylidene Fluoride Nanofibers Hybridized by Polytetrafluoroethylene Nanoparticles for High-Efficiency Air Filtration. ACS applied materials & interfaces 2016, 8 (36), 23985-23994.
Wang, Z. et al. Porous Bead-on-String Poly (Lactic Acid) Fibrous Membranes for Air Filtration. Journal of colloid and interface science 2015, 441, 121-129.
Wang, Z.-F. et al. Aspirin-triggered Lipoxin A4 attenuates mechanical allodynia in association with inhibiting spinal JAK2/STAT3 signaling in neuropathic pain in rats. Neuroscience 2014, 273, 65-78.
Ward AR, et al. Comparison of Heating of Nonliving Soft Tissue produced by 45 kHz and 1 MHz Frequency Ultrasound Machines. J Orthop Sports Phys Ther. 1996;23(4):258-266.
Wartzek, et al. Triboelectricity in capacitive biopotential measurements. IEEE Trans. Biomed. Eng. 58, 1268-1277 (2011).
Who, "New report calls for urgent action to avert antimicrobial resistance crisis," <https://www.who.int/news/item/29-04-2019-new-report-calls-for-urgent-action-to-avert-antimicrobial-resistance-crisis> dated Apr. 29, 2019.
Who. Coronavirus Disease (Covid-19) Advice for the Public: When and How to Use Masks. https://www.who.int/emergencies/diseases/novel-coronavirus-2019/advice-for-public/when-andhow-to-use-masks (Updated Dec. 2021) (12 pages).
Who. Shortage of Personal Protective Equipment Endangering Health Workers Worldwide. https://www.who.int/news/item/03-03-2020-shortage-of-personal-protective-equipment-endangering-health-workers-worldwide. Mar. 3, 2020 (3 pages).
Wiese, A. D.; et al. Opioid analgesics and the risk of serious infections among patients with rheumatoid arthritis: a self-controlled case series study. Arthritis & rheumatology 2016, 68, (2), 323-331.
Witzleb et al. Exposure to chromium, cobalt and molybdenum from metal-on-metal total hip replacement and hip resurfacing arthroplasty. Acta Orthop. 77, 697-705 (2006).

(56) References Cited

OTHER PUBLICATIONS

Woltjer et al. (2016) "Optimization of piezo-MEMS layout for a bladder monitor" in 2016 IEEE International Ultrasonics Symposium (IUS) (IEEE, 2016), pp. 1-4.

Wu, S. et al. Surface Modification of Pure Magnesium Mesh for Guided Bone Regeneration: In Vivo Evaluation of Rat Calvarial Defect. Materials 12, 2684 (2019).

Wynn, R. F. et al. A small proportion of mesenchymal stem cells strongly expresses functionally active CXCR4 receptor capable of promoting migration to bone marrow. Blood 104, 2643-2645 (2004).

Xin et al., A Site-Specific Integrated Column 2. 3GFP Reporter Identifies Osteoblasts Within Mineralized Tissue Formed In Vivo by Human Embryonic Stem Cells. Stem cells translational medicine 3, 1125-1137 (2014).

Xiong, Z.-C. et al. Flexible Hydroxyapatite Ultralong Nanowire-Based Paper for Highly Efficient and Multifunctional Air Filtration. Journal of Materials Chemistry A 2017, 5 (33), 17482-17491.

Xu X, et al. Strong vibration-catalysis of ZnO nanorods for dye wastewater decolorization via piezo-electro-chemical coupling. Chemosphere. 2018;193:1143-1148.

Xu, E. G.; et al.Preventing Masks from Becoming the Next Plastic Problem. Frontiers of environmental science & engineering 2021, 15 (6), 125.

Yang, M.; et al. Is Pm1 Similar to Pm2. 5? A New Insight into the Association of Pm1 and Pm2. 5 with Children's Lung Function. Environment International 2020, 145, 106092.

Yoshimoto, I. et al. Development of layered PLGA membranes for periodontal tissue regeneration. Dent. Mater. 34, 538-550, (2018).

You H., et al. Strong piezo-electrochemical effect of multiferroic BiFeO3 square micro-sheets for mechanocatalysis. Electrochem Commun. 2017;79:55-58.

Yu, J.; et al. Glucose-responsive insulin patch for the regulation of blood glucose in mice and minipigs. Nature Biomedical Engineering 2020, 1-8.

Yu, Y. et al. Multifunctions of dual Zn/Mg ion co-implanted titanium on osteogenesis, angiogenesis and bacteria inhibition for dental implants. Acta Biomater. 49, 590-603 (2017).

Zhang, H. et al. Drug delivery systems for differential release in combination therapy. Expert opinion on drug delivery 2011, 8, (2), 171-190.

Zhang, J. et al. Biodegradable Electrospun Poly (Lactic Acid) Nanofibers for Effective Pm 2.5 Removal. Macromolecular Materials and Engineering 2019, 304 (10), 1900259.

Zhang, Q.; et al. Transboundary Health Impacts of Transported Global Air Pollution and International Trade. Nature 2017, 543 (7647), 705-709.

Zhang, R. et al. Nanofiber Air Filters with High-Temperature Stability for Efficient Pm2. 5 Removal from the Pollution Sources. Nano letters 2016, 16 (6), 3642-3649.

Zhang, S.; et al. Spider-Web-Inspired Pm0. 3 Filters Based on Self-Sustained Electrostatic Nanostructured Networks. Advanced Materials 2020, 32 (29), 2002361.

Zhang, Y. et al. Preparation of Nanofibrous Metal-Organic Framework Filters for Efficient Air Pollution Control. Journal of the American Chemical Society 2016, 138 (18), 5785-5788.

Zhao et al., Electrospun poly(L-lactic acid) nanofibers for nanogenerator and diagnostic sensor applications. Macromol. Mater. Eng. 302, 1600476 (2017).

Zhou Y, Niu C, Ma B, Xue X, Li Z, Chen Z, Li F, Zhou S, Luo X, Hou Z: Inhibiting PSMalpha-induced neutrophil necroptosis protects mice with MRSA pneumonia by blocking the agr system. Cell Death Dis 2018, 9(3):362.

Zhu X, et al. Nanomedicine in the management of microbial infection—Overview and perspectives. Nano Today. 2014;9(4):478-498.

\* cited by examiner

BIODEGRADABLE PIEZOELECTRIC ULTRASONIC TRANSDUCER SYSTEM

CROSS-REFERENCE TO RELATED APPLICATIONS

This application is a non-provisional of and claims the benefit of U.S. Provisional Patent Application No. 62/812,491, filed on Mar. 1, 2019, the contents of which are incorporated herein by reference.

COLOR DRAWINGS

The patent or application file contains at least one drawing executed in color. Copies of this patent or patent application publication with color drawings will be provided by the Office upon request and payment of the necessary fee.

BACKGROUND

Piezoelectric materials, a type of "smart" material that generates electricity while deforming and vice versa, are used in many important implantable medical devices such as sensors, transducers, and actuators. Piezoelectric sensors have been used along with medical catheters inside the body to monitor important physiological pressures such as intracranial pressure, blood pressure, bladder pressure, etc.

More recently, researchers have developed implanted piezoelectric ultrasonic transducers to disrupt the blood-brain barrier (BBB) and facilitate the delivery of drugs into the brain. The BBB, which is composed of tight junctions between the endothelial cells in the blood vessels of the brain, prevents most therapeutics from accessing the brain tissue and thus is a major hurdle for the treatment of brain diseases (e.g., cancers). There are several established methods for opening the BBB, which include solvent, adjuvant, acoustic wave, lipidization, and osmostic pressure; ultrasound (US) or acoustic waves have been extensively studied and shown to be safe and the most effective tool. However, the use of external US is limited to small animals with thin skull bones. Since the human skull is thick and absorbs more than 90% of US energy, it requires a large and bulky array of external US transducers, a complicated energy-focusing operation, and a tedious MM (magnetic resonance imaging) monitoring procedure. This extensive process would be useful for a single treatment like viral gene delivery-based approaches. However, in certain applications such as chemotherapy, research has shown the opening of the BBB requires repetitive treatment. As such, implanted US transducers (e.g., Sonocloud) have emerged as an alternative, which can repeatedly induce low-intensity sonication deep inside brain tissue at a precise location to open the BBB without causing any damage to the surrounding brain tissue.

Unfortunately, all of the aforementioned pressure sensors and US transducers rely on conventional piezoelectric materials such as PZT (lead zirconate titanate), PVDF (polyvinylidene fluoride), ZnO (zinc oxide), etc., which are either toxic and/or non-degradable. Thus, these piezoelectric devices pose significant concerns regarding safety after implantation and require a removal surgery, which is invasive and deleterious to directly interfaced organs or tissues.

SUMMARY

The disclosure provides a powerful biodegradable and biocompatible piezoelectric nanofiber platform for significant medical implant applications, including a highly sensitive, wireless, biodegradable force sensor for the monitoring of physiological pressures, and a biodegradable ultrasonic transducer for the delivery of drugs across the blood-brain barrier. Built upon materials commonly utilized in medical implants, the devices can self-degrade, causing no harm to the body, and avoid any invasive removal surgeries.

The disclosed device is completely biodegradable after a controllable lifetime and biocompatible (as it is made of commonly implanted medical materials, such as PLLA, PLA, PCL, PLGA, Mg, Mo, candelilla wax, etc., which have been used extensively in many FDA-approved erodible implants). Therefore, it doesn't need an invasive removal surgery which is required for other implanted ultrasonic transducers. Other transducers also rely on toxic materials such as PZT (which contains lead) and therefore there is significant concern with potential leakage and toxicity of the currently-used ultrasonic device.

The device is an ultrasonic transducer that can be implanted inside the body (e.g., brain, bone, knee, abdomen etc.) and can generate ultrasonic waves or acoustic pressures that are used to stimulate the opening of biological barriers (such as the blood brain barrier, intestinal epithelial barrier, etc.) to facilitate the diffusion of drugs and increase uptake of drugs into organs (e.g., brain, bone, blood, etc.). The ultrasound generated by the device can also be used to disrupt and kill cancerous tissues through heat generated by cavitation. Wireless communication is another possible application of this device. Specifically, the transducer can be used to emit ultrasonic waves, and could therefore serve as a replacement for all non-degradable RF wireless devices (e.g., NFC, Bluetooth, etc.) or non-biodegradable ultrasonic transceivers, which are intensively used for telecommunication in current electronic implants.

In one embodiment, the disclosure provides a biodegradable ultrasonic transducer comprising a first biodegradable metal electrode, a second biodegradable metal electrode, a biodegradable piezoelectric material positioned between the first biodegradable metal electrode and the second biodegradable metal electrode, and an encapsulation layer covering the first biodegradable metal electrode, the second biodegradable metal electrode, and the biodegradable piezoelectric material.

In another embodiment, the disclosure provides a biodegradable ultrasonic transducer system comprising a biodegradable ultrasonic transducer described above and a coil coupled to the first biodegradable metal electrode and the second biodegradable metal electrode.

In a further embodiment, the disclosure provides a method of constructing a biodegradable ultrasonic transducer. The method comprises electrospinning PLLA nanofiber to form a nanofiber mesh by rotating a drum at a speed of between 2,000-4,000 rpm, annealing the nanofiber mesh between 100° C.-110° C. for a first period of time, annealing the nanofiber mesh between 155° C.-165 C for a second period of time, sandwiching the annealed nanofiber mesh between a first biodegradable metal electrode and a second biodegradable metal electrode to form a sensor, electrically coupling the sensor to a wire, and encapsulating the sensor and the wire with a biodegradable medical polymer.

In another embodiment, the disclosure provides a method of delivering a therapeutic through a blood-brain barrier. The method comprises applying the biodegradable ultrasonic transducer that was constructed by the method described above to a craniotomy defect, transmitting an ultrasonic wave signal through the wire, and delivering a pulsed acoustic pressure to the defect.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
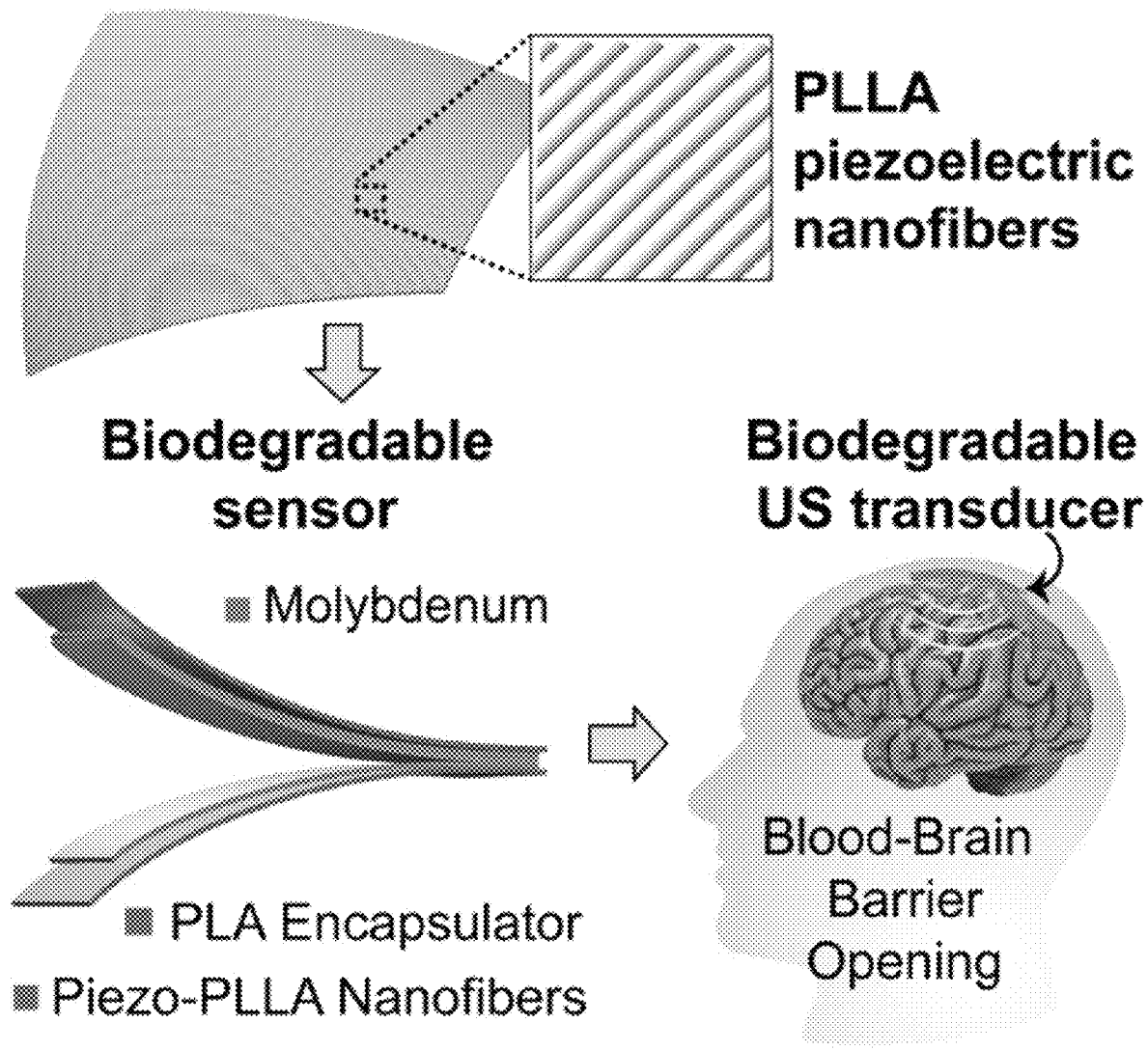
FIG. 1 illustrates PLLA nanofibers with highly controllable and excellent piezoelectric performance for biodegradable implanted piezoelectric devices. The image at Top is a simplified schematic of the treated piezoelectric PLLA nanofibers. The image at Bottom Left is the schematic of a biodegradable pressure sensor and ultrasound (US) transducer. The image at Bottom Right is a schematic illustrating the biodegradable US transducer, implanted inside the brain, which can repeatedly induce US to open the blood-brain barrier (BBB) and facilitate the delivery of drugs into the brain.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Piezoelectricity is a phenomenon which allows materials to convert deformation into electricity and vice versa. Piezoelectric materials are often used for force/pressure sensors, transducers, and generators. The materials can be fabricated into nano- and microstructures and interfaced with soft tissues to monitor biological forces. Since piezoelectric materials can generate electricity from mechanical impact, they can serve as appealing sensing materials, alternative to the described passive semiconductors and capacitive polymers, for self-powered force sensors. However, commonly used piezoelectric materials such as lead zirconate titanate (PZT) and polyvinylidene difluoride (PVDF) contain toxic or non-biodegradable components, respectively, and thus are not favorable for implantation inside the human body.

Poly-L-lactic acid (PLLA), a biocompatible and biodegradable polymer has recently been found to exhibit piezoelectricity when appropriately processed, thereby offering an excellent platform to construct safer, biodegradable piezoelectric implants, which can avoid problematic removal surgeries. The material exhibits shear piezoelectricity due to electrical polarity present in the carbon-oxygen double-bond branching off from the polymer backbone chain. Although possessing a modest piezoelectric response (5-15 pC/N), PLLA has a low dielectric constant, which allows the material to perform the same energy-conversion efficacy as the common piezoelectric polymer PVDF. By creating a multilayered structure, one can achieve even higher piezoelectricity from PLLA, with an "effective" conversion efficiency, similar to that of ceramic PZT.

Previously, thermally stretched, compression-molded PLLA bulk films were employed to create a biodegradable piezoelectric force sensor. However, stretched PLLA bulk films pose several problems, including low reproducibility, film rigidity, and modest piezoelectric constants (~5 to 12 pC/N) (20, 21), which render the bulk PLLA films useless for actuators, transducers or highly sensitive pressure sensors. Recently, biodegradable amino acid crystals (e.g., glycine) have been reported with an excellent piezoelectric constant. However, it is challenging to fabricate these powder-based materials into functional films and orient the crystals in a repeatable manner to obtain a controllable piezoelectric performance for device applications. A few researchers have utilized electrospinning to create flexible PLLA piezoelectric nanofiber films, but the reported works struggle with major limitations. First, these reports lack appropriate material processing to stabilize the nanomaterial or utilize the shear-piezoelectric mode (i.e., d14) of PLLA for an optimal piezoelectric performance. Consequently, the PLLA nanofibers can only produce small, unstable electrical signals under applied force. Second, the measured electrical signals are often mixed with other noises caused by friction between the rough nanofiber film and metal electrodes, commonly known as the triboelectric effect. Third, there is no report on the ability to control the piezoelectric performance of the PLLA nanofibers. These major drawbacks collectively restrict applications of this nanomaterial. As a result, there are only a few reported applications of piezoelectric PLLA nanofibers for non-degradable and non-implantable force sensors or energy harvesters.

The disclosure provides a strategy for materials processing, device assembly, and electronic integration to 1) achieve biodegradable and biocompatible piezoelectric PLLA nanofibers with a highly controllable, efficient, and stable piezoelectric performance, and 2) demonstrate biodegradable, safe piezoelectric devices built upon this powerful nanomaterial (FIG. 1). First, it is demonstrated that a biodegradable force sensor, made with the PLLA nanofiber film, possesses higher sensitivity and flexibility than that of the reported thermally stretched PLLA bulk film and can be used to wirelessly monitor vital physiological pressures. Second, it is demonstrated that the same PLLA nanofiber sensor acts as a biodegradable ultrasonic transducer that can be implanted into the brain to open the BBB and safely self-degrade, causing no harm to the body. Despite several achievements in the field of biodegradable electronics, this report introduces a biodegradable, highly efficient piezoelectric US transducer, which is only made of materials commonly utilized in medical implants to facilitate the BBB opening for the delivery of drugs into the brain.

In order to improve the piezoelectric response of PLLA, the two major material properties that need to be addressed are the crystallinity and orientation of the polymer chains. By improving these properties, the carbon-oxygen double bonds (C=O) present in the helical PLLA backbone become aligned resulting in an inherent net polarization, and a well-documented shear piezoelectric response under applied force. The PLLA nanofibers are made using an electrospinning process. The speed of the rotating drum was varied from 300 to 4,000 rpm, while other parameters such as the voltage applied to the needle, distance to collector, needle gauge, flow rate, and solution concentrations were held constant. This resulted in PLLA nanofiber mats with different levels of fiber orientation. The nanofiber mat samples initially made by the electrospinning setup are highly amorphous and unstable, as seen by the DSC (differential scanning calorimetry). Therefore, the samples were carefully annealed and slowly cooled down in two serial steps at 105° C. and 160.1° C. to improve the crystallinity. After these annealing processes, the crystallinities of the processed nanofiber samples appear to be in about the same range of 70% to 88% (see DSC data of FIG. 2 (at A)). The nanofiber films, collected at smaller spin speeds, have lower levels of fiber alignment. Therefore, the 300 rpm electrospun PLLA sample was selected as a negative control due to its lower crystallinity and poor fiber orientation, which results in little-to-no piezoelectric effect. X-ray diffraction (XRD) data show that all of the samples are predominantly (200) and (110) (miller index for crystal planes) crystal phases, indicating the presence of β-form crystal structures, which is the piezoelectric phase of PLLA. Additionally, as seen in the 2D XRD images of FIG. 2 (at B), electrospinning with a faster collector speed improves the orientation of the crystal domains in each nanofiber. The fiber alignment over the entire film also appeared to increase with faster collector speeds, as seen in the scanning electron microscopy (SEM) images (FIG. 2 (at C)). However, macroscopic orientation of the PLLA fibers and the molecular alignment are also related to the jet speed (dictated by applied voltage used for electrospinning). By tuning the jet speed to match the drum speed, the optimal piezoelectric PLLA film can be generated.

Figure 2:
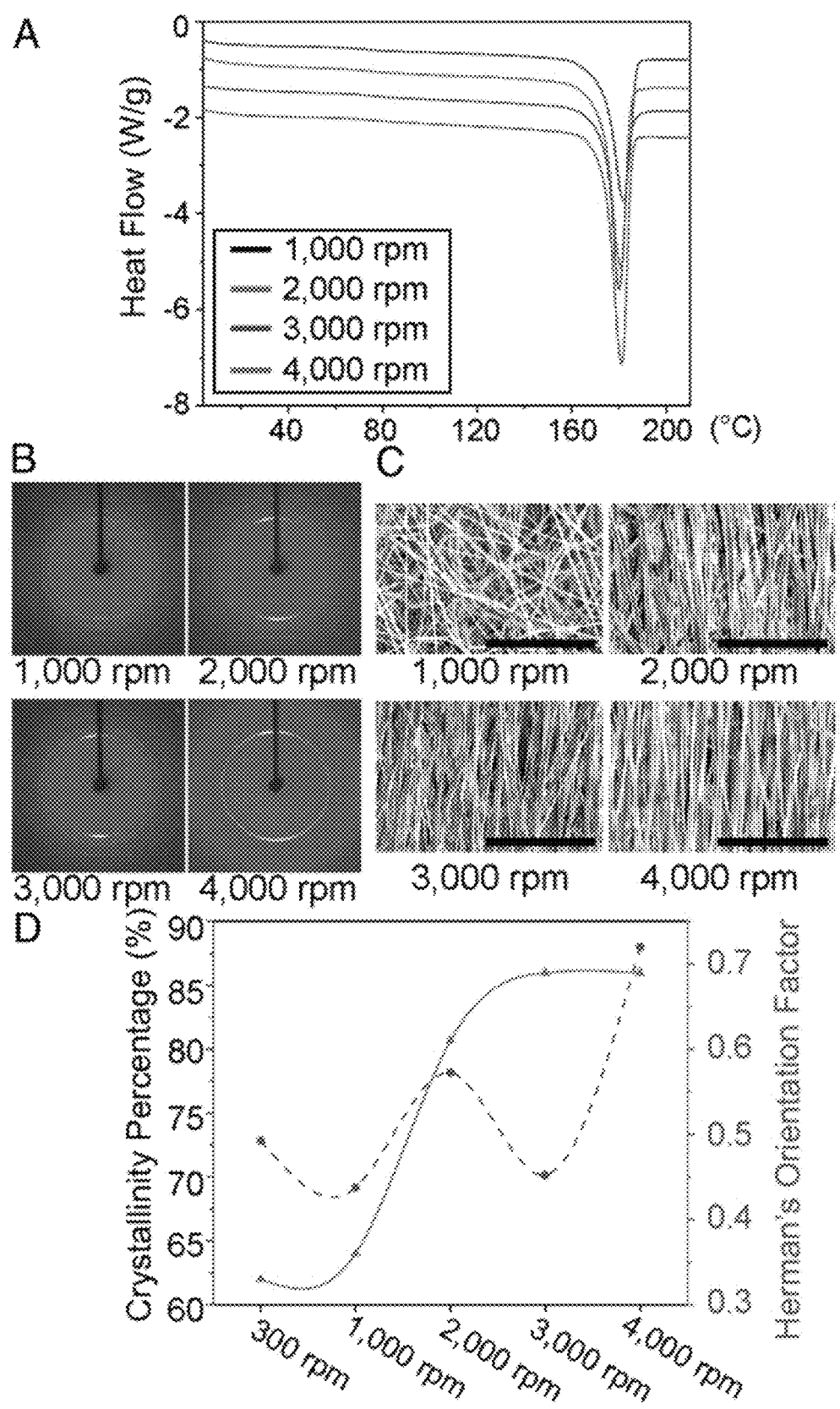
FIG. 2 illustrates material characterization of the electrospun PLLA. (A) Results from differential scanning calorimetry (DSC) of electrospun PLLA nanofiber films collected at different spin speeds. (B) The 2D X-ray diffraction (2D XRD) images show orientation of crystal domains inside the electrospun PLLA nanofibers, made with different collection speeds. (C) Scanning electron microscopy (SEM) images show PLLA nanofiber alignment with different collection speeds. (Scale bars, 40 μm.) (D) Graphical summary illustrating the trend that, as the PLLA nanofibers are collected at faster speeds, the Herman orientation factor (i.e., crystal alignment) and crystallinity percentage generally increase.

Estimation of the crystallinity (using DSC) and Herman's orientation factor (using 2D XRD) for the electrospun PLLA samples is described in FIG. 2 (at D), which shows that improving the collector drum speed generally results in higher crystallinity and crystal alignment in the nanofibers. Thus, by tailoring the collector and jet speeds, the piezoelectricity of the nanofibers can be controlled.

The piezoelectric performance of the PLLA nanofiber films was assessed through an impact test (i.e., generation of voltage under impact force) and an actuation test (i.e., displacement under an applied electric field). To create the PLLA sensor for these tests, the PLLA film was annealed and cut at a 45° angle relative to the fiber direction to utilize shear piezoelectricity by maximizing shear force under an applied normal force. The fully treated and cut PLLA films possess a stable, efficient, and highly controllable piezoelectric performance, which has not been achieved by previous reports for the PLLA nanofibers. The films were then sandwiched between aluminum foil electrodes and Kapton tape. For impact testing, the PLLA sensor was subjected to a consistent force induced by an actuator, which was integrated with a dynamic force sensor and driven by a defined voltage waveform. The charge output from the PLLA sample was measured with an electrometer. All of the sensors had the same area of 161.29 mm$^2$ and thicknesses in the range of 19 to 28 Additionally, prior to fabrication of the sensors, all of the films are soaked in deionized water to minimize the influence of the triboelectric effect.

Figure 3:
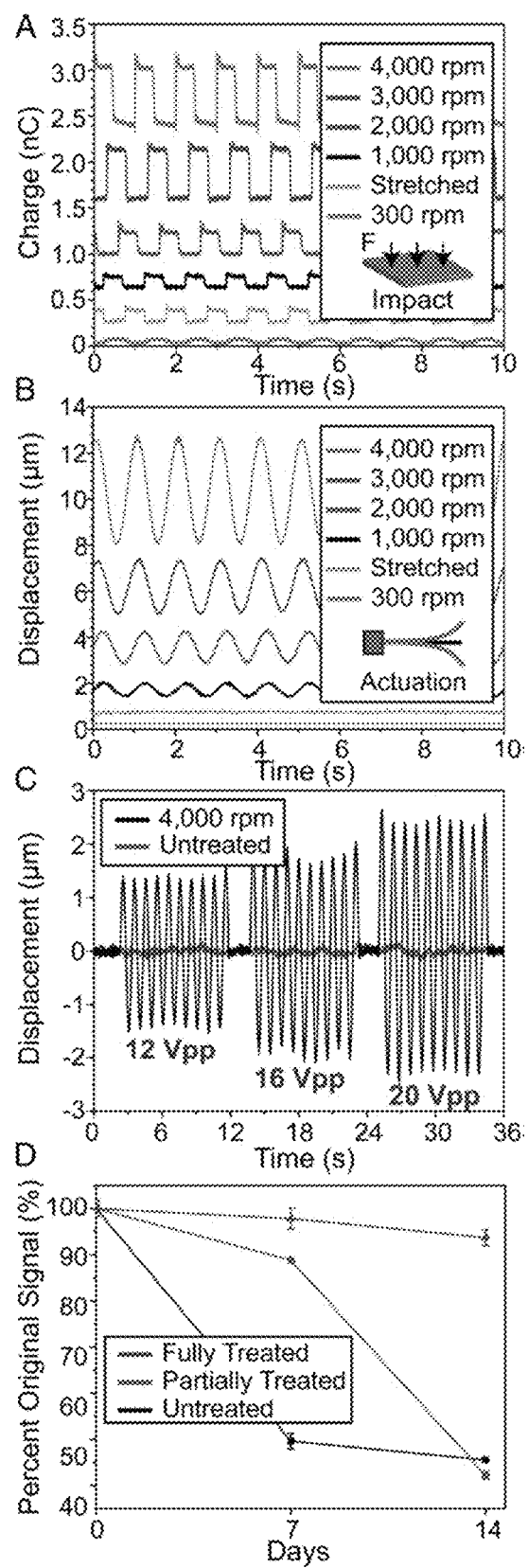
FIG. 3 illustrates piezoelectric characterization of the treated PLLA nanofiber films. (A) Charge output from stretched, bulk piezo-PLLA (yellow) and treated electrospun PLLA, collected at different speeds, under the same impact force. (B) Displacement of stretched, bulk PLLA (yellow) and treated electrospun PLLA, collected at different speeds, under the same voltage (20 $V_{pp}$) at 1 Hz. (C) Displacement of 300 rpm PLLA negative-control sample (red) and 4,000 rpm PLLA (black), under increasing magnitudes of voltage at 1 Hz. (D) Comparison of the piezoelectric performance for 3,000 rpm electrospun PLLA samples annealed under different conditions over a 14-d period.

FIG. 3 (at A) illustrates charge outputs from the PLLA samples subjected to a 30-N impact force. The signals generated from the 6 treated PLLA samples clearly show the electrospun sample collected at 4,000 rpm has the largest charge output of about 0.9 nC while the 300 rpm sample exhibits little-to no charge output (~0.1 nC). The highly aligned nanofiber film, collected at 3,000 and 4,000 rpm drum speeds, noticeably outperforms the bulk piezoelectric PLLA film [annealed and stretched with a 3.5 draw ratio (DR)]. All open-circuit voltage outputs for these piezoelectric nanofiber films were reversible when the electrode connections were swapped, indicating that the PLLA is truly polarized, and that the measured signal is minimally influenced by triboelectricity.

The impact measurement was also repeated using dry films, and the resulting data was used to estimate the shear piezoelectric coefficient ($d_{14}$) for all of the samples. Using the measured mechanical properties of the PLLA films, the piezoelectric constant of the samples was roughly estimated; the 4,000 rpm sample appears to exhibit a $d_{14}$ of −19 pC/N, while the conventional bulk PLLA film only exhibits a $d_{14}$ of −12 pC/N. This indicates that the processing of PLLA nanofibers significantly improves the material's shear piezoelectric response. Furthermore, cutting the PLLA films at 45° angles to utilize shear piezoelectricity was also justified by comparing the charge outputs of a 0° and 45° cut film under the same applied force. For the actuation measurement, a treated PLLA film (1.27 cm×1.27 cm) was sandwiched in the center of aluminum foil electrodes (9.53 mm×9.53 mm). A controlled voltage waveform was then applied to the sensor, and the displacement in the exposed right corner of the sample was measured using a laser displacement sensor. As seen in FIG. 3 (at B), the treated PLLA nanofiber samples vibrate with the same frequency (1 Hz) as the applied sinusoidal voltage waveform (20 $V_{pp}$). The 4,000 rpm electrospun sample again exhibits the greatest displacement (~4.5 μm), while the stretched 3.5 DR bulk film and 300 rpm electrospun samples exhibited no measurable displacement. This result confirms the superior piezoelectric performance of the highly aligned nanofiber film. In addition, as the amplitude of the applied voltage increases, the amplitude of displacement for the electrospun films also increases, and the displacement is frequency dependent (FIG. 3 (at C). Piezoelectric performance in the treated PLLA nanofiber film is also stable. This advantage is significant as there has been little research to avoid depolarization of the PLLA nanofibers over time. Indeed, as seen in FIG. 3 (at D), only an electrospun sample (3,000 rpm) that underwent the full annealing processes (i.e., annealed at both 105° C. and 160.1° C.) has a stable piezoelectric output under the same applied force (~30 N) for 7 d, with a marginal loss (~6%) in signal at 14 d. In contrast, the untreated (i.e., not annealed) and partially treated (i.e., annealed only at 105° C.) samples rapidly lose their performance and are therefore not stable for long-term implant applications.

After verifying the piezoelectric effect of the PLLA nanofibers, a biodegradable force sensor was created by using the nanofibers, molybdenum (Mo) electrodes, and encapsulating untreated PLLA layers (FIG. 1). PLLA or PLA are common biodegradable polymers used in Food and Drug Administration (FDA)-approved implanted tissue scaffolds, bone screws, and drug carriers. Molybdenum is a common nutrient and a biodegradable metal. A biodegradable piezoelectric force sensor was previously reported, however, the device was based on the stretched PLLA bulk film, which is less flexible, exhibits much lower piezoelectric performance, and consequently offers lower sensitivity for force detection.

Figure 4:
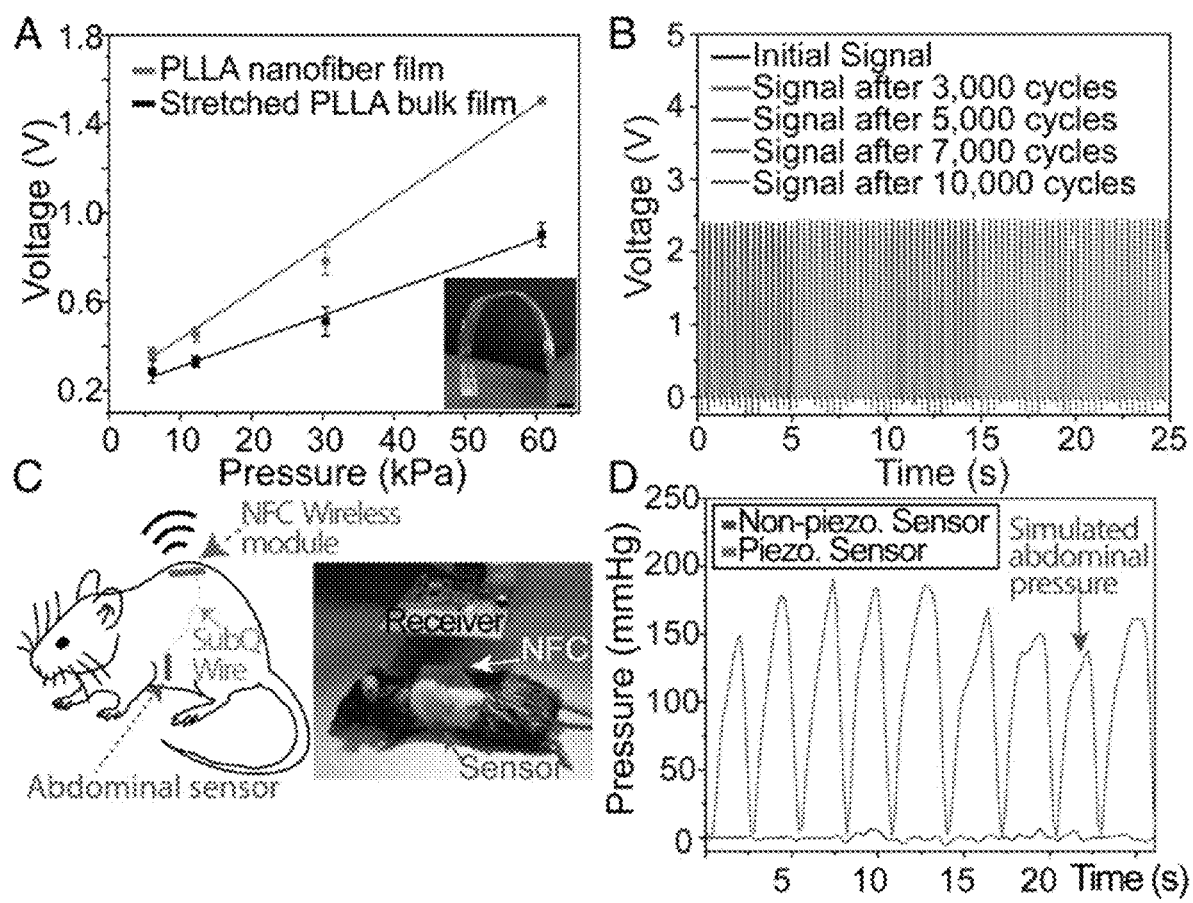
FIG. 4 illustrates a wireless, biodegradable PLLA-nanofiber force sensor. (A) Comparison of calibration curves for a biodegradable sensor using stretched, bulk piezo-PLLA film (black) and a 4,000 rpm electrospun PLLA nanofiber film (red). Inset shows the optical image of the biodegradable and flexible force sensor, made from the PLLA nanofibers. (Scale bar, 5 mm.) (B) Output from a charge amplifying circuit connected to a 4,000 rpm electrospun, biodegradable PLLA sensor that is subjected to 10,000 cycles of a 10-N force. (C) Simplified schematic of the implanted, wireless pressure sensor in a mouse (Left) and optical image of a mouse receiving the wireless PLLA sensor implanted (Right). NFC, near-field communication chip. (D) Comparison of the simulated abdominal pressure signals, wirelessly recorded from an implanted biodegradable PLLA nanofiber sensor using a 300 rpm negative control (black) and a 4,000 rpm film (red).

FIG. 4 (at A) clearly illustrates this by showing that the slope of a calibration curve for a biodegradable sensor made with a treated 4,000 rpm electrospun PLLA film is 1.8 times steeper than that of a sensor, using a conventional thermally stretched, bulk PLLA film (DR=3.5). However, when compared to a sensor made of a common non-degradable piezoelectric PVDF-TrFE film (which exhibits a higher $d_{33}$ of approximately 34 pC/N), the biodegradable 4,000 rpm electrospun PLLA sensor appears to produce lower-amplitude signals under the same applied force. It is also shown that the charge output from the same 4,000 rpm sensor is stable for over 10,000 cycles of the same impact force (10 N). Not only was the 4,000 rpm electrospun film more sensitive, but its higher crystallinity did not appear to result in any significant changes to the degradation rate when compared to the bulk PLLA piezoelectric film. Without being encapsulated, the PLLA films exhibited a reduction in piezoelectricity after being exposed to aqueous environments due to plastic deformation under an applied load. It was then demonstrated that the nanofiber sensor can be used to monitor intra-abdominal pressure in a mouse.

The sensor (5 mm×5 mm) was fully implanted into the abdominal cavity of a mouse and connected to a small printed circuit board (PCB) via a subcutaneous (s.c.) biodegradable wire made of Mo and coated in PLLA. The PCB contains a charge amplifying circuit, a wireless near-field communication (NFC) chip and a commercial antenna. The entire PCB was sealed inside an 18 mm×14 mm PDMS (polydimethylsiloxane) box and subcutaneously implanted at the back of the animal (FIG. 4 (at C)). Thus, the abdominal sensor and the connecting wires can self-degrade, while the non-degradable PCB could be easily removed at the end of the sensor's lifetime in a minimally invasive manner. The mouse's abdomen, filled with saline solution, was then manually stimulated to generate an internal fluid pressure, which mimicked a change in intra-abdominal pressure. A clearly distinguishable signal (FIG. 4 (at D)) was wirelessly measured while the mouse's abdomen was periodically depressed and relaxed. The measured pressure signal was then compared to the signal generated by a 300 rpm PLLA sensor (negative control) to verify the signal was not generated by triboelectricity and motion artifacts of the wires (FIG. 4 (at D)). These results clearly demonstrate the potential of the biodegradable PLLA sensor for monitoring vital physiological pressures inside the body.

Figure 5:
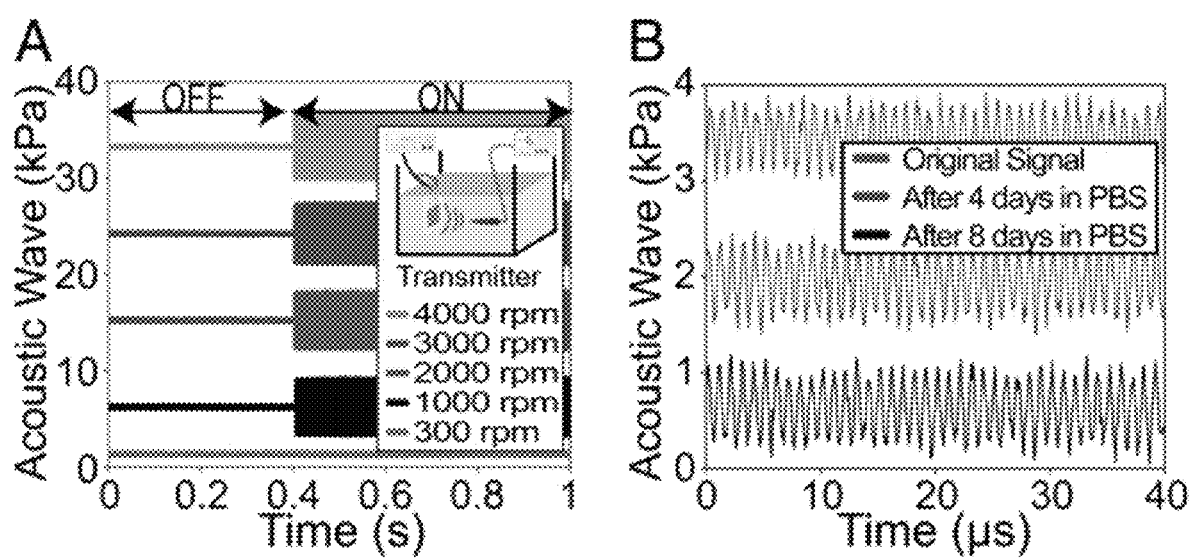
FIG. 5 illustrates US characterization of the biodegradable PLLA-nanofiber transducer. (A) The output pressure from the transducer with different electrospinning speeds under the same input voltage. The Inset is the simplified schematic of the experiment. (B) Output pressure from a biodegradable US transducer made from 4,000 rpm electrospun PLLA under the same input voltage after different days in PBS at 37° C.

In addition to monitoring intra-abdominal pressure, it was demonstrated that the same PLLA nanofiber sensor can also be used as a biodegradable ultrasound (US) transducer. The PLLA nanofibers' ability to transmit or receive ultrasonic waves was tested. During US transmission testing (FIG. 5 (at A, Inset)), a capsule hydrophone was used to measure the acoustic pressure. The PLLA device was driven by a function generator to produce a continuous ultrasonic wave at 1 MHz. As seen in FIG. 5 (at A), there was no signal detected when the function generator was "off." When the generator was "on," all PLLA transducers generated distinct acoustic waves while the 300 rpm sample (negative-control sample, non-piezoelectric) resulted in only noise. The trend is similar in the US receiving test; in all of these experiments, the highly aligned 4,000 rpm sample provided the highest conversion signals. Interestingly, the PLLA transducers can act as speakers to generate audible sounds and even play music.

A degradation experiment was conducted and demonstrated that a transducer, using encapsulating layers of untreated PLLA (100 μm thick), can have a lifetime of up to 8 d in phosphate buffer saline (PBS) at 37° C. (FIG. 5 (at B)). Longer functional lifetimes can certainly be achieved by engineering the properties [i.e., thickness or molecular weight (MW)] of the encapsulating PLLA layers or using other biodegradable encapsulating polymers.

Figure 6:
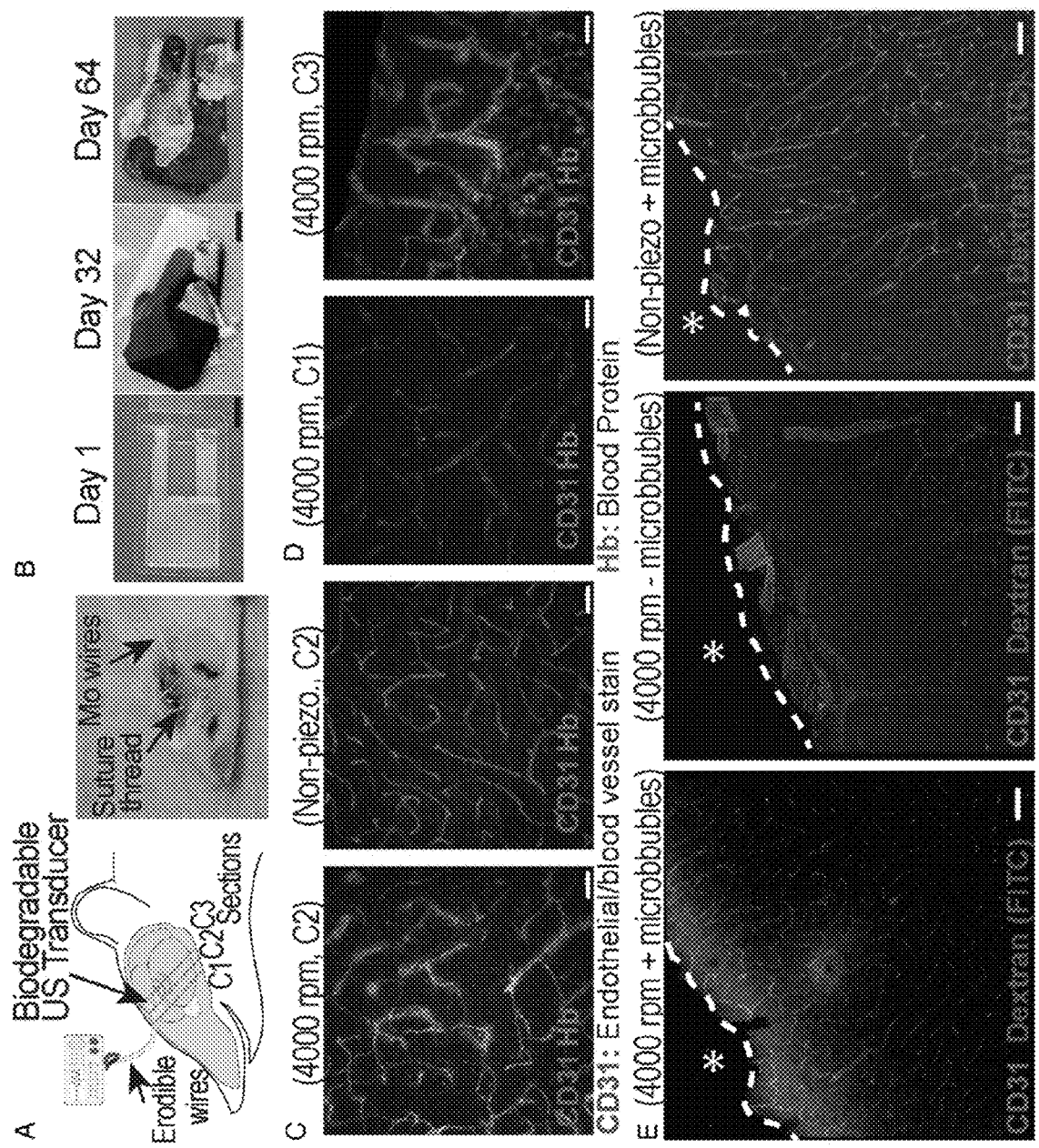
FIG. 6 illustrates an in vivo experiment to demonstrate the application of PLLA nanofiber transducer for the BBB opening and drug delivering. (A) The schematic (Left) and optical image (Right) of the in vivo experiment. (B) The optical images of a typical biodegradable US transducer at different days in the buffered solution at an accelerated-degradation temperature of 70° C. (Scale bars, 5 mm.) (C) Representative images showing the autofluorescent signal of blood protein at the coronal section (C2) from the brains of mice that received US from the 4,000 rpm PLLA transducer (Left) and the 300 rpm PLLA negative-control transducer (Right). (D) Representative images show the blood protein signal at different coronal sections of the same mouse brain receiving the US treatment. Section C3 (Right) is closer to the implanted transducer, while section C1 (Left) is far away from the implanted US transducer, serving as an internal control. (Scale bars in C and D, 30 μm.) (E) Representative images show the signal of dextran (FITC) at the coronal sections from the brains of mice that received different treatments and samples. The dashed lines show the boundary between the brain and the biodegradable device. The asterisk (*) shows the position of the implanted device. (Scale bars, 50 μm.)

As proof-of-concept on a potential application of the biodegradable transducer, the PLLA device was employed, made of 4,000 rpm nanofiber samples, for disruption of the BBB in vivo. The experiment is illustrated in FIG. 6 (at A). A 5 mm×5 mm biodegradable US transducer, which was connected to flexible, biodegradable PLLA-encapsulated Mo wires, was placed on a craniotomy defect in a mouse skull. The spatial pressure field of the biodegradable transducer was recorded. The transducer was operated at 1 MHz to generate an acoustic pressure of 0.3 MPa (rarefaction pressure value) in a series of 2 shots lasting 30 s, with a 30-s break between each shot. The device functioned well in its predefined lifetime and eventually self-degraded (FIG. 6 (at B)). The brains were processed for fluorescence analysis of bloodborne elements to gauge leakage of the BBB. Two indicators of leakage were intentionally chosen in order to reflect the relative degree of BBB disruption. Tissue autofluorescence at 488 nm was associated with the presence of the 64.5 kDa (in MW) blood protein hemoglobin, which has been suggested to leak across a disrupted BBB. As seen in FIG. 6 (at C), a noticeable halo of autofluorescence (green stain) could be seen around various microvessels (red stain) in the brains of mice sonicated by the 4,000 rpm transducer. In contrast, no similar signal was observed from the same coronal sections (C2) of the control mouse, sonicated by the 300 rpm non-piezoelectric control sample. Additional brain sections of the control mouse (receiving the non-piezoelectric device) were documented. As further illustrated in FIG. 6 (at D), for the mice that received US treatment, the closer the coronal sections were to the implanted transducer, the more disrupted vessels were associated with autofluorescent signals. This serves as an internal control and clearly shows the local US-induced BBB opening. The BBB opening was again confirmed by immunofluorescence analysis on the leakage of the serum protein IgG (~150 kDa).

To further certify the potential application of the biodegradable device for delivering therapeutics or pharmaceutical agents through the BBB, another in vivo animal model was performed. The procedure of this experiment was similar to the previous experiment except that the dextran (3 kDa, FITC, Lysine Fixable; Thermo Fisher) as a drug model was retro-orbitally injected into the mice after the sonication process. Additionally, another control group in which mice did not receive the microbubbles before sonication was added to this experiment in order to validate the effect of microbubbles in the BBB opening. As seen in FIG. 6 (at E, Left), a remarkable level of green signal (FITC) was found around the microvessels in the brain of mice that received the treatments by the 4,000 rpm transducer and microbubbles. It is noticeable that the intensity of the FITC signal is reduced at deeper areas of the brain. On the other hand, no green signal was detected from the same coronal sections of the two control samples, FIG. 6 (at E, Center and Right). If higher output acoustic pressure and wireless powering are needed for the US transducer, the device can be fabricated with multiple layers of PLLA nanofiber films and utilize the inductive coupling effect.

Finally, to demonstrate the biocompatibility of the PLLA nanofiber devices, these devices were implanted subcutaneously into the backs of mice and the intracranial cavity of rats for histology analysis. The histological images from both experiments showed that the device elicits minimal fibrosis and immune response after implantation for 2 and 4 wk. Collectively, these results illustrate that the biodegradable PLLA transducer can be implanted safely into the brain to locally and effectively open the BBB, which could facilitate the delivery of drugs into the brain for the treatment of various brain diseases or disorders. Built upon materials commonly utilized in medical implants, the transducer can self-degrade, causing no harm to the body, and avoid any invasive brain surgery for removal.

Figure 7:
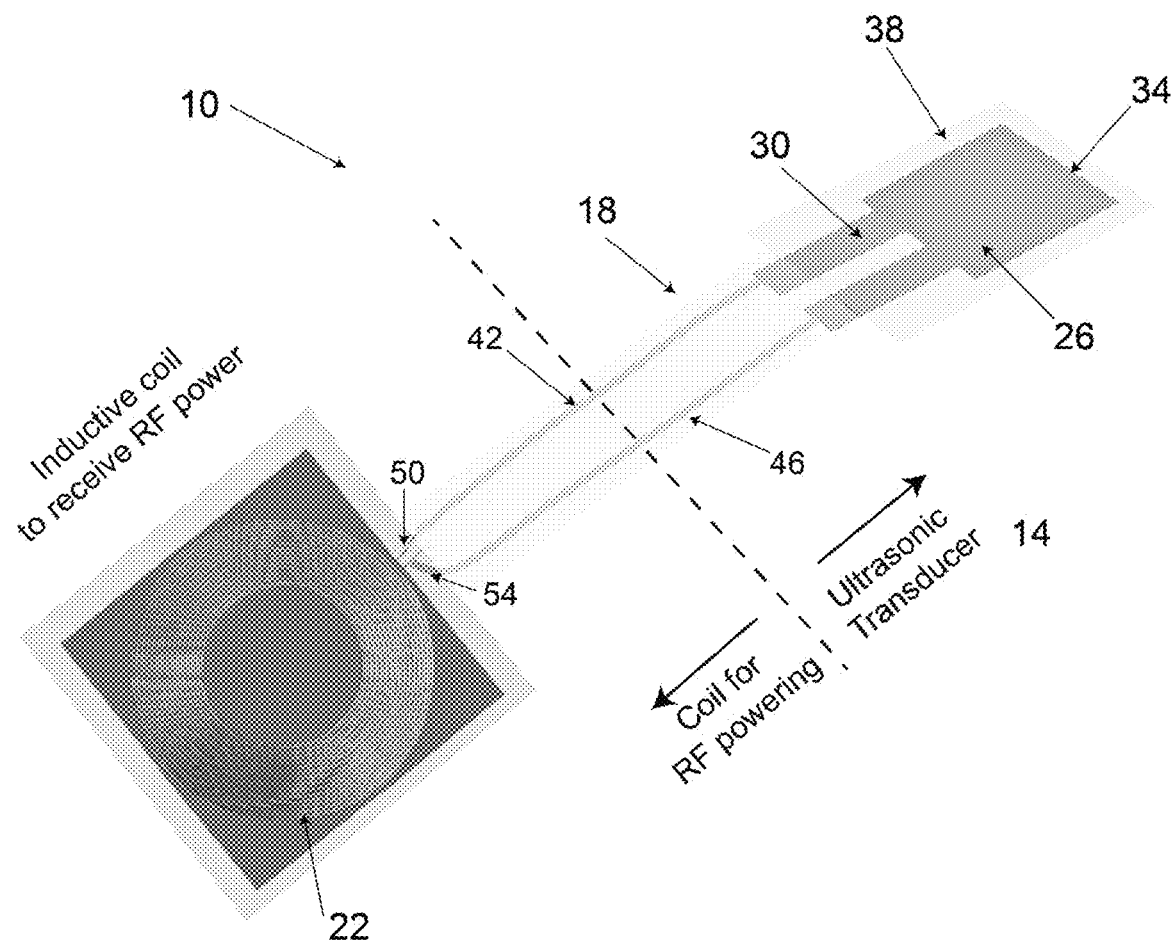
FIG. 7 is a schematic of a biodegradable ultrasonic transducer system as disclosed herein.
Figure 8:
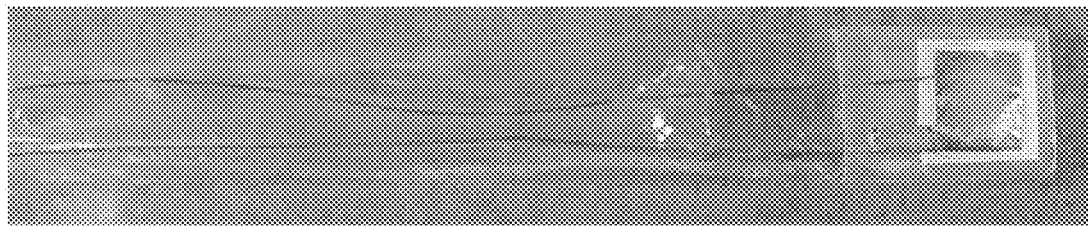
FIG. 8 illustrates a biodegradable ultrasonic transducer as disclosed herein.

FIG. 7 illustrates a schematic of a biodegradable piezoelectric ultrasonic transducer system 10. The biodegradable piezoelectric ultrasonic transducer system 10 includes a transducer 14, a link 18, and a coil 22. FIG. 8 also illustrates a constructed biodegradable piezoelectric ultrasonic transducer 14 and a link 18. In one construction, the size of the ultrasonic patch is 5 mm×5 mm. The transducer 14 comprises a first biodegradable metal electrode 26 and a second biodegradable metal electrode 30. A biodegradable piezoelectric material 34 is positioned between the first electrode 26 and the second electrode 30.

The biodegradable piezoelectric material 34 is positioned between the electrodes 26, 30 can be PLLA, silk, glycine, etc., which are all biodegradable and safe for use inside the body. The piezoelectric material 34 may have an area greater than or equal to the area of the electrodes 26, 30. As illustrated in FIGS. 7-8, the piezoelectric material 34 includes an area slightly greater than the area of the electrodes 26, 30 as the piezoelectric material 34 extends beyond the edges of the electrodes 26, 30. In one construction, the piezoelectric material PLLA can be treated by mechanical stretching and thermal annealing to obtain stable piezoelectric properties (Eli Curry et al. Biodegradable piezoelectric force sensor, PNAS, 2018). The PLLA can also be processed into a stable piezoelectric material through electrospinning and thermal treatment. The piezoelectric film can be prepared by electrospinning a 4% w/v solution of PLLA dissolved in a 1:4 mixture of N,N-Dimethylformamide (DMF) and dichloromethane (DCM). The solution is pumped at a constant rate of 2 ml/hr through a 22-gauge needle with a 14 kV (kilovolts) DC voltage applied to it (Eli Curry et al. Biodegradable piezoelectric nanofiber based transducer, PNAS Jan. 7, 2020 117 (1) 214-220). This electrified solution is then sprayed at a ground aluminum drum rotating at speeds from 300-4,500 rpm (rotations per minute). This results in a nanofiber mat of PLLA (diameter ~300 nm) with varying degrees of alignment based on rotating drum speed. These fibrous mats are then annealed at 105° C. for 10 hr and allowed to cool to room temperature. They are then annealed at 160° C. for 10 hr and allowed to cool to room temperature. Finally, the electrospun films are cut at a 45° angle relative to the oriented direction in order to harvest the shear piezoelectric signal of the film.

The metal electrodes 26, 30 can comprise different biodegradable metals, including: Molybdenum (Mo), Magnesium (Mg), Iron (Fe), Zinc (Zn) conducting polymers, etc. or an alloy of any of the previously mentioned metals. The electrodes 26, 30 and piezoelectric material 34 are covered in an encapsulation layer 38 with a biodegradable medical polymer. The encapsulation layer 38 can comprise poly (lactic acid) (PLA), poly(lactic-co-glycolic acid) (PLGA), candelilla wax, polycaprolactone (PCL), metals such as Mo or other suitable biodegradable polymer.

The link 18 includes a first wire 42 and a second wire 46 coupled to the transducer 14. The first wire 42 is coupled to the first biodegradable metal electrode 26 and the second wire 46 is coupled to the second biodegradable metal electrode 30. The first wire 42 and the second wire 46 comprise Mo in one construction and is encapsulated inside a flexible biodegradable encapsulation layers made of PLA, poly(glycerol sebacate) (PGS), poly(octamethylene maleate (anhydride) citrate) (POMaC), PLGA, or other suitable biodegradable polymer. As illustrated in FIG. 7, the transducer 14 and the link 18 are encapsulated with the same encapsulation layer 38. By controlling the thickness, molecular weight, or by using different polymers, the functional-lifetime of the transducer 14 can be engineered and pre-defined prior to implantation.

The inductive coil 22 is coupled to the link 18. The inductive coil 22 includes a first end 50 coupled to the second wire 46 and a second end 54 coupled to the first wire 46. The inductive coil 22 comprises Mg or Mo which can receive power supplied through a resonant inductive coupling effect from an outside transmitting coil to provide power to the ultrasonic transducer 14. The inductive coil 22 is encapsulated inside a biodegradable polymer of PLA or PGS or PoMac or PLGA, or another suitable biodegradable polymer. The inductive coil 22 also is biodegradable, similar as the transducer 14. As illustrated in FIG. 7, the transducer 14, the link 18, and the coil 22 are encapsulated with the same encapsulation layer 38.

In an alternative construction, the transducer 14 can be connected to a non-degradable link and a non-degradable coil or other electronics to receive power. During the implantation of such a system, the transducer 14 can be implanted into the tissue that it needs to target (e.g., inside the skull, close to dura mater to open the blood brain barrier) while the non-degradable electronics (in replacement of the inductive coil 22 in FIG. 7) can be implanted subcutaneously and far away from the delicate tissue to be targeted. After the transducer 14 is used, the non-degradable electronics can be removed in a minimally-invasive manner while the transducer 14 will self-degrade without the need to be removed thus minimizing surgical risk.

In another alternative construction, a transcutaneous wire can be connected to the transducer 14 and an external power source can be used to power the transducer. The wire will be very small. After the functional lifetime of the transducer 14, the transcutaneous wires can be removed through a minimally invasive surgery while leaving the biodegradable transducer intact within the delicate/important tissue.

The biocompatibility of the transducer 14 (including piezoelectric PLLA, encapsulating layer PLA, and electrode Mo) inside the brain has been tested. The result after one month shows minimal immune rejection and an excellent biocompatibility of the device.

Figure 9:
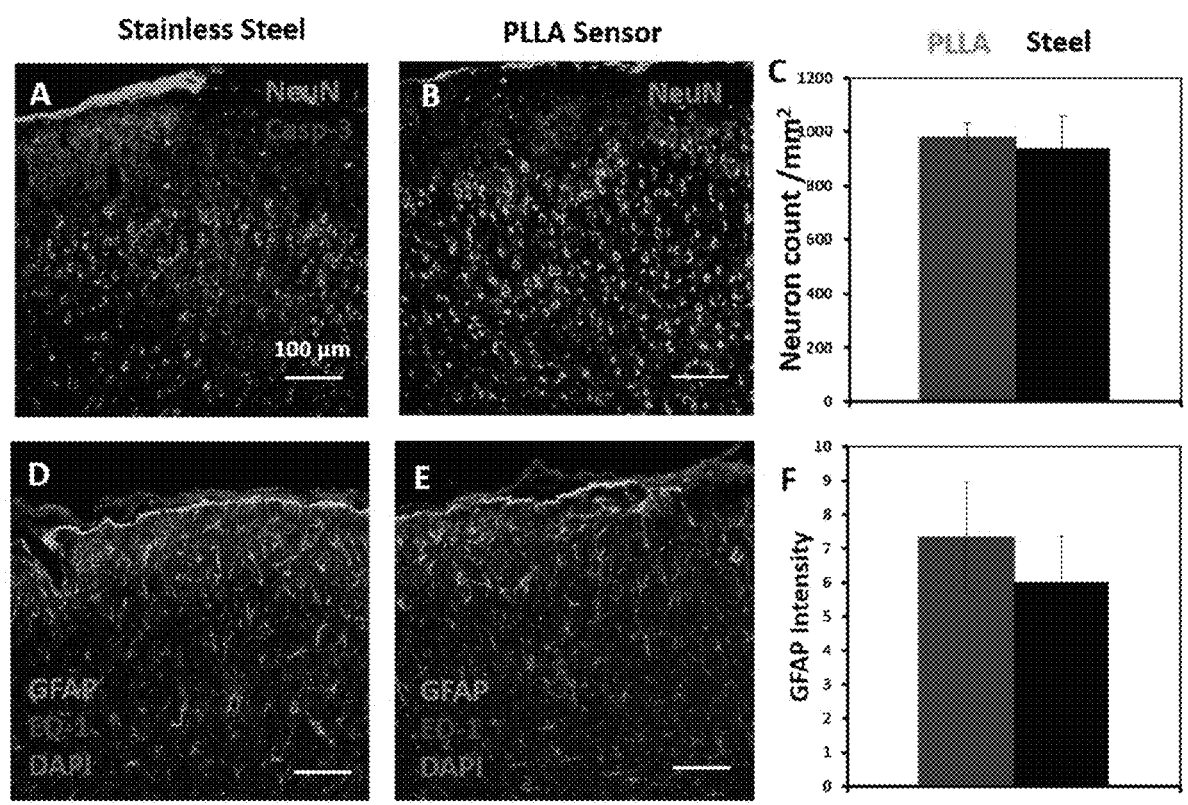
FIG. 9 illustrates neuronal health after 2 weeks implantation inside rat brain. At 2 weeks, no differences in neuronal density or GFAP expression were observed between the PLLA sensor and stainless steel implants, based on the immunofluoresecent images of NeuN/Caspase-3 (A and B) and GFAP/ED-1 (D and E) images and the quantifications of Neuronal counts (C) and GFAP intensity within 100 μm from the implant at the brain surface, normalized to the deeper region of the same images (F). Two animals and 4 sections each were used. Data presented as mean±SEM).
Figure 10:
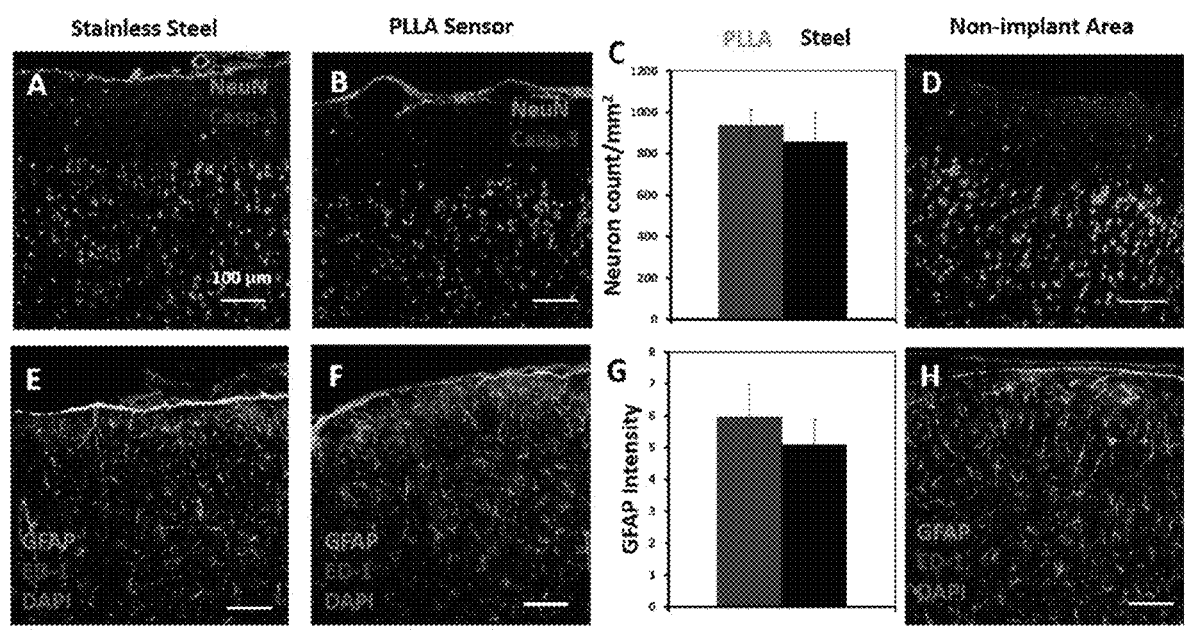
FIG. 10 illustrates neuronal health after 4 week implantation inside rat brain. At 4 weeks, no differences in neuronal density or GFAP expression were observed between the PLLA sensors and stainless-steel implants, based on the immunofluorescent images of NeuN/Caspase-3 (A and B) and GFAP/ED-1 (E and F) and the quantification of neuronal counts (C) and GFAP intensity within 100 μm from the implant at the brain surface, normalized to the deeper region of the same images (G). For quantification, two animals and 4 sections each were used. Data presented as mean±SEM. Additionally, examples of non-implanted control region (D and H) showed similar distribution of NeuN, Caspase-3 (D), GFAP and ED-1 positive cells (H) as the implanted regions. These data clearly describe biocompatibility of our PLLA transducer and its degradation byproducts at least for 4 week implantation inside brain.

To examine if implantation of the transducer 14 has caused any inflammatory or damaging reactions on the underlying cortical tissues, the neuronal density and health underneath the transducer and stainless steel samples at week 2 and week 4 were compared (see FIG. 9 and FIG. 10). The distribution of neurons is similar between the control and the PLLA device (FIG. 9 (at A and B) and FIG. 10 (at A and B)), with no significant difference in neuronal density (FIG. 9 (at C) and FIG. 10 (at C)).

Moreover, all neurons appear healthy, based on the lack of NeuN/Caspase-3 co-localization. Qualitatively, the distribution of GFAP positive cells (astrocytes) and ED-1 positive cells (macrophage in the meningeal layer and activated microglia in the brain) also appear similar between the stainless steel and the sensor-implanted regions, and also between the sensor-implanted regions and non-implanted control regions (i.e., regions without any implants). Quantification of the GFAP intensity showed no significant difference between the two implanted areas (FIG. 9 (at F) and FIG. 10 (at F)), and also between the implanted areas and the areas without any implant. Taken together, this histological study suggests that the implanted PLLA-transducer is benign and does not cause harmful host tissue response inside the brain for the periods examined.

In another biocompatibility test, the PLLA transducer 10 (with the same structure and materials including piezoelectric PLLA sandwiched between Mo electrodes and encapsulated in PLA) was implanted inside a subcutaneous area of mice and the results show a very minimal inflammation or mild immune response to the implant.

Figure 11:
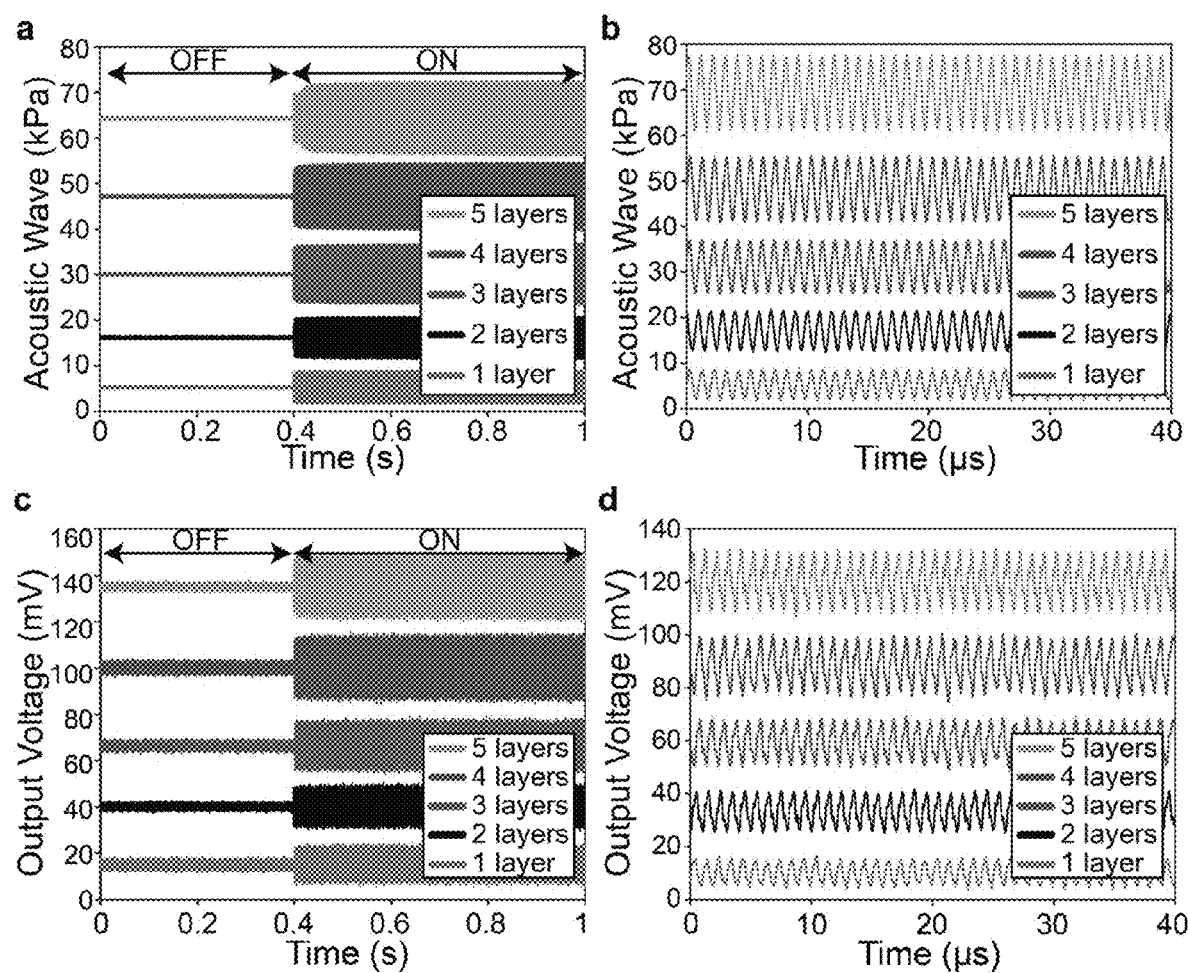
FIG. 11 graphically demonstrates the ability of transmitting and receiving ultrasonic waves of the biodegradable ultrasonic transducer of FIG. 8 with different number of piezoelectric PLLA layers. In order to characterize the transmitting properties of the transducer, the acoustic pressure generated from the biodegradable transducers are measured from the capsule hydrophone (A and B). Additionally, the output voltages of the multilayers biodegradable transducers, subjected to a 10 kPa acoustic pressure at 1 MHz, are demonstrated (C and D).

It has been shown that the transducer 14 can generate as well as receive ultrasonic wave in a wide range of frequencies. FIG. 11 shows that a transducer 14 with a varying number of piezoelectric PLLA layers can generate different acoustic pressures under the same applied input voltage at 1 MHz or provide different output voltage values (Vpp) when being subjected to the same applied acoustic pressure (generated by a commercial ultrasonic transmitter) at 1 MHz frequency in water. Increasing the number of PLLA layers boosts the sensitivity or the power of the transducer.

Figure 12:
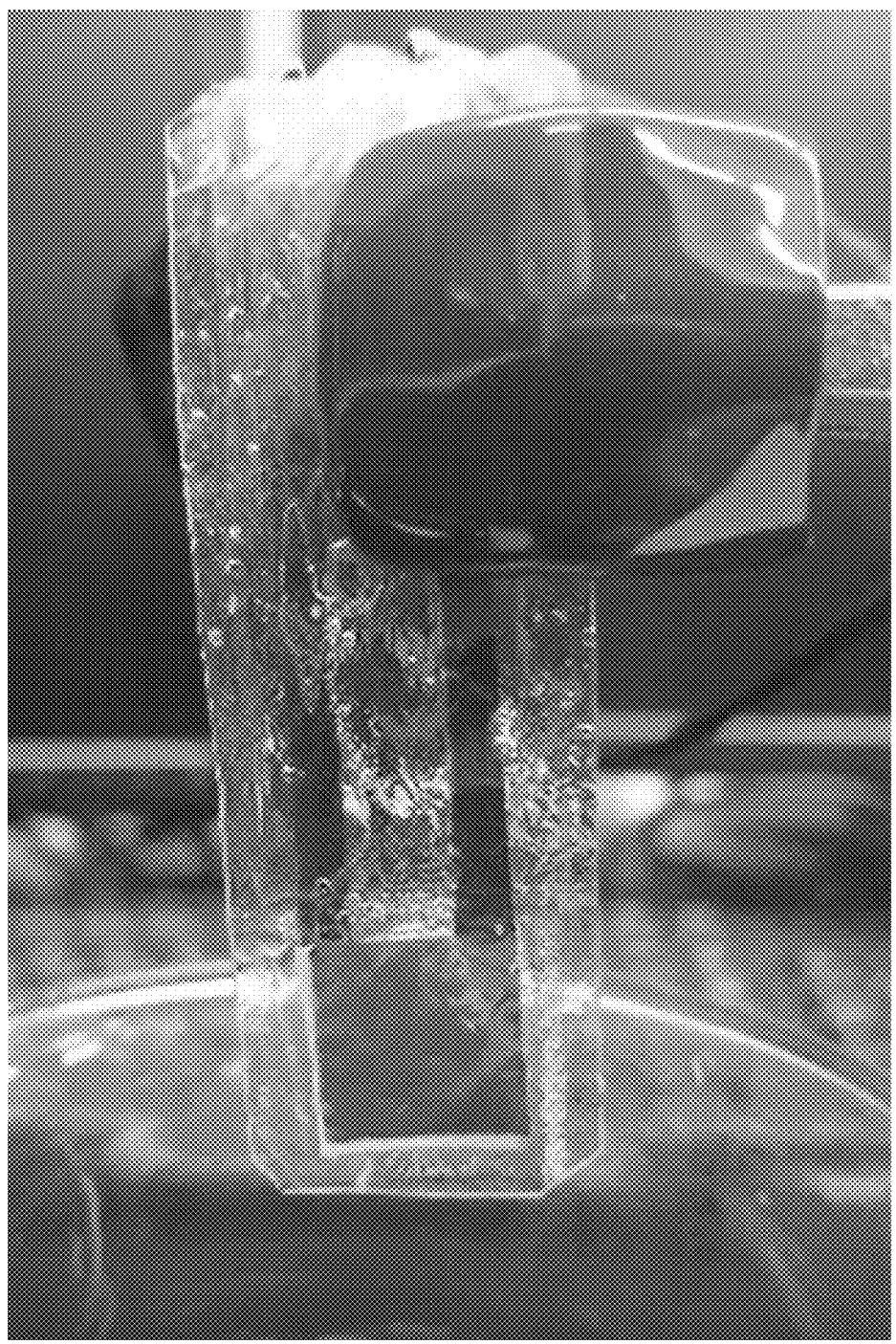
FIG. 12 shows that the device generates an audible sound at a frequency of 9 kHz before degrading inside a buffer solution. This shows the ability of the device to vibrate and generate acoustic waves under applied electrical voltage.

It is also shown that the transducer 10 can generate sound under an applied electrical signal. Under an AC input voltage at 9 kHz, the device can generate an audible sound. The transducer 10 degrades afterward as illustrated in FIG. 12.

Various features and advantages of the invention are set forth in the following claims.

What is claimed is:

1. A biodegradable ultrasonic transducer comprising:
a first biodegradable metal electrode;
a second biodegradable metal electrode;

a biodegradable piezoelectric material positioned between the first biodegradable metal electrode and the second biodegradable metal electrode;

a first link comprised of a biodegradable material, the first link coupled to the first biodegradable metal electrode and a coil;

a second link comprised of a biodegradable material, the second link coupled to the second biodegradable metal electrode and the coil; and an encapsulation layer covering the first biodegradable metal electrode, the second biodegradable metal electrode, the biodegradable piezoelectric material, the first link, and the second link, wherein the biodegradable ultrasonic transducer is configured for implantation near a target and to receive power through the first link and the second link to generate ultrasound waves for delivery to the target.

2. The transducer of claim 1, wherein the biodegradable piezoelectric material comprises poly (L-lactic acid) (PLLA).

3. The transducer of claim 1, wherein the encapsulation layer comprises a biodegradable medical polymer.

4. The transducer of claim 3, wherein the biodegradable medical polymer is poly(lactic acid) (PLA).

5. The transducer of claim 1, wherein the biodegradable piezoelectric material has a piezoelectric constant greater than 12 pC/N.

6. The transducer of claim 1, wherein the biodegradable piezoelectric material has a perimeter greater than a perimeter of the first biodegradable metal electrode or the second biodegradable metal electrode.

7. A biodegradable ultrasonic transducer system comprising:

a biodegradable ultrasonic transducer of claim 1; and a coil coupled to the first biodegradable metal electrode and the second biodegradable metal electrode.

8. The system of claim 7, wherein the coil is coupled to the first biodegradable metal electrode with a first wire and to the second biodegradable metal electrode with a second wire.

9. The system of claim 8, wherein the first wire and the second wire comprise Molybdenum (Mo).

10. The system of claim 8, wherein the coil is covered with the encapsulation layer.

11. The system of claim 9, wherein the coil is covered with the encapsulation layer.

* * * * *